United States Patent
Nakagawa et al.

[11] Patent Number: 5,225,406
[45] Date of Patent: Jul. 6, 1993

[54] 1-CARBOXY-1-VINYLOXYIMINO AMINOTHIAZOLE CEPHALOSPORIN DERIVATIVES

[75] Inventors: Susumu Nakagawa; Ryuji Mitomo; Koji Yamada; Norikazu Otake; Fumio Nakano; Akira Asai; Satoru Kuroyanagi; Yoshiharu Tanaka; Moriaki Ishikawa; Ryosuke Ushijima, all of Okazaki, Japan

[73] Assignee: Banyu Pharmaceutical Co., Ltd., Tokyo, Japan

[21] Appl. No.: 753,943

[22] Filed: Sep. 3, 1991

Related U.S. Application Data

[62] Division of Ser. No. 265,458, Oct. 13, 1988, Pat. No. 5,084,453.

[51] Int. Cl.$^5$ .................. C07D 501/36; A61K 31/545
[52] U.S. Cl. ..................... 514/206; 540/227; 540/222; 540/225
[58] Field of Search ............ 540/221, 222, 227; 514/206

[56] References Cited

U.S. PATENT DOCUMENTS 5,049,558 9/1991 Bradbury et al. ............... 540/222
5,084,453 11/1992 Nakagawa et al. ............... 540/222

Primary Examiner—Nicholas S. Rizzo
Attorney, Agent, or Firm—Oblon, Spivak, McClelland, Maier & Neustadt

[57] ABSTRACT

The present invention relates to a compound having the formula:

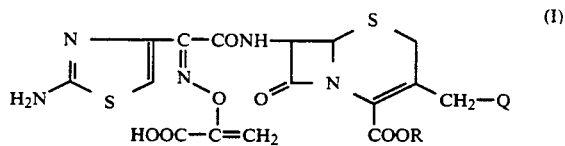

wherein R is a hydrogen atom, a carboxyl-protecting group or a negative charge and Q is a hydrogen atom, a halogen atom, a hydroxyl group, an acetoxy group, a carbamoyloxy group, an azide group, a substituted or unsubstituted quarternary ammonio group or a substituted or unsubstituted heterocyclic thio group having at least one hetero atom selected from the group consisting of a nitrogen atom, an oxygen atom, and a sulfur atom, or a non-toxic salt or physiologically hydrolyzable non-toxic ester thereof; a process for producing it; and an antibacterial agent comprising it as an active ingredient.

Further, the present invention also relates to a compound having the formula:

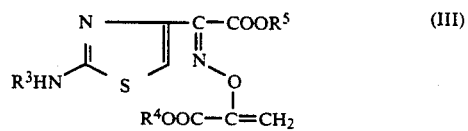

wherein $R^3$ is a hydrogen atom or an amino-protecting group, and each of $R^4$ and $R^5$ which may be the same or different is a hydrogen atom or a carboxyl-protecting group, or a salt thereof; and a process for producing it.

7 Claims, No Drawings

1-CARBOXY-1-VINYLOXYIMINO AMINOTHIAZOLE CEPHALOSPORIN DERIVATIVES

This is a division, of application Ser. No. 07/265,458, filed on Oct. 13, 1988, now U.S. Pat. No. 5,084,453.

TECHNICAL FIELD

The present invention relates to novel cephalosporin derivatives, a process for their production, antibacterial agents containing them as active ingredients and intermediates for their production.

BACKGROUND TECHNOLOGY

Heretofore, a number of compounds have been synthesized which have a 2-substituted oxyiminoacetamide group as a side chain at the 7-position of the cephem nucleus. For example, there may be mentioned a 2-(2-aminothiazol-4-yl)-2-substituted oxyiminoacetamide group, a 2-(2-aminooxazol-4-yl)-2-substituted oxyiminoacetamide group, a 2-(5-amino-1,2,4-thiadiazol-3-yl)-2-substituted oxyiminoacetamide group, a 2-(furyl-2-yl)-2-substituted oxyiminoacetamide group or a 2-substituted phenyl-2-substituted oxyiminoacetamide group. As publications which disclose such compounds, for example, Japanese Unexamined Patent Publications No. 52083/1975, No. 102293/1977, No. 116492/1977, No. 137988/1978, No. 154786/1979, No. 157596/1979, No. 154980/1980, No. 86187/1981, No. 59895/1982, No. 99592/1982, No. 158769/1982, No. 192394/1982, No. 8087/1983 and No. 174387/1983, and The Chemical Society of Japan, Vol. 5, p.785–805 (1981), may be mentioned. It is disclosed that such compounds exhibit antibacterial activities against Gram-positive bacteria and Gram-negative bacteria including Pseudomonas aeruginosa thus suggesting that they have excellent antibacterial activities and a broad antibacterial spectrum.

In addition to the above publications, as the prior arts concerning the present invention, Japanese Unexamined Patent Publications No. 9296/1979, No. 162592/1983, No. 108792/1984, No. 130294/1984, No. 34972/1985, No. 67483/1985 and No. 97982/1985, may be mentioned. In the claims of such publications, as substituents of the 2-(2-aminothiazol-4-yl)-2-substituted oxyiminoacetamide group at the 7-position of the cephem nucleus, a number of substituents are mentioned including an alkyl group and an alkenyl group. Further, the description of the alkenyl group is general referring, for example, to an alkenyl group which may be substituted, or a substituted unsubstituted $C_2$–$C_8$ alkenyl group. However, the alkenyl group suggested by the specific disclosure and examples in the specifications is an unsubstituted alkenyl group such as a vinyl group or an allyl group. Further, as the alkenyl group substituted by a carboxyl group, there is only a 1-carboxylate allyl group, and there is no disclosure or suggestion concerning the 1-carboxy-1-vinyl group in the above prior art references. Further, with respect to the prior art relating to intermediates, a number of 2-substituted oxyiminoacetic acid derivatives have been synthesized as the acyl side chain acid at the 7-position of the cephem nucleus. As such an acyl side chain acid, for example, a 2-(2-aminothiazol-4-yl)-2-substituted oxyiminoacetic acid, a 2-(thiazol-4-yl)-2-substituted oxyiminoacetic acid, a 2-(2-aminooxazol-4-yl)-2-substituted oxyiminoacetic acid, a 2-(5-amino-1,2,4-thiadiazol-3-yl)-2-substituted oxyiminoacetic acid, a 2-(furyl-2-yl)-2-substituted oxyiminoacetic acid or a 2-(substituted phenyl)-2-substituted oxyiminoacetic acid, may be mentioned. As the publications describing such 2-substituted oxyiminoacetic acid compounds, for example, Journal of the Japanese Chemical Society, p.785–804 (1981), the J. of Antibiotics, Vol. 34, p.1447–1455 (1981), ditto Vol. 35, p.712–720 (1982), ditto Vol. 36, p.1205–1210 (1983), ditto Vol. 37, p.532–571 (1984) and ditto Vol. 39, p.111–127 and p.404–414 (1986) may be mentioned. As the substituents of such substituted oxyimino groups, for example, lower alkyl, lower alkenyl, lower alkynyl, aralkyl and aryl groups which may have one or more substituents such as a hydroxyl group, a carboxyl group, a carbamoyl group, a cyano group, an amino group, a halogen atom, an alkyl group and an aryl group, are generally known.

Further, a 2-(1-vinyloxyimino)acetic acid derivative having a vinyl group as a substituent of the substituted oxyimino group is described in Japanese Unexamined Patent Publication No. 22392/1979 (corresponding to Ger. Offen., 2,831,332; Chem. Abstr., 90-168630n), and synthesized as shown by the following reaction scheme.

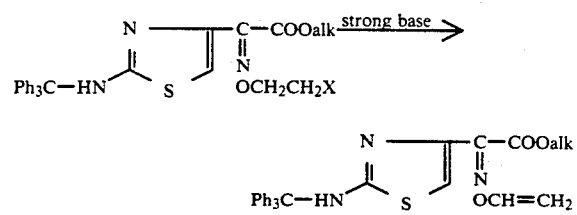

In the formulas, X is a chlorine atom, a bromine atom or an iodine atom and alk is an alkyl group having from 1 to 4 carbon atoms.

This publication discloses only the 2-(1-vinyloxyimino)acetic acid derivative, and no synthesis or suggestion for a 2-(1-carboxy-1-vinyloxyimino)acetic acid derivative of the present invention is given.

β-lactam antibiotics exhibit selective toxicity only against bacteria and give no substantial affects against animal cells, and they have been widely used for the treatment of infectious diseases caused by bacteria, as antibiotics having no substantial side effects. Thus, they are highly useful drugs. However, in recent years, the isolating frequency of resistant Gram-positive bacteria and resistant glucose non-fermentative Gram-negative rods, as causative organisms tends to increase. Therefore, it is desired to increase the activities of antibiotics against such bacteria.

It is an object of the present invention to provide novel cephalosporin derivatives having excellent antibacterial activities. Various cephalosporin derivatives have been synthesized which have a 2-substituted oxyiminoacetamide group at the 7-position of the cephem nucleus. With respect to a compound having a 1-carboxy-1-vinyloxyimino group as such substituted oxyimino group, however, there is no disclosure in patent specifications, not to mention its synthesis.

Namely, the compound of the present invention having a 2-(2-aminothiazol-4-yl)-2-(1-carboxy-1-vinyloxyimino)acetamide group at the 7-position of the cephem nucleus is a novel compound not disclosed in literatures. The present inventors have found that the compound of the present invention have strong antibacterial activities against sensitive or resistant Gram-negative bacteria and Gram-positive bacteria and excellent stability against β-lactamase. The present invention has been accomplished on the basis of the discovery.

Further, the present inventors have conducted extensive researches to develop 2-(2-aminothiazol-4-yl)-2-(1-carboxy-1-vinyloxyimino)acetic acid derivatives and a process for their production. As the results, it has been found that when the 2-(2-aminothiazol-4-yl)glyoxylic acid derivative of the formula VI is reacted with O-(1-carboxy-1-vinyl)hydroxylamine derivative of the formula V, and if necessary, the protecting group is removed, it is possible to obtain the compound of the present invention having the formula III in good yield. The present invention has been accomplished on the basis of the discovery.

DISCLOSURE OF THE INVENTION

The present invention provides a compound having the formula:

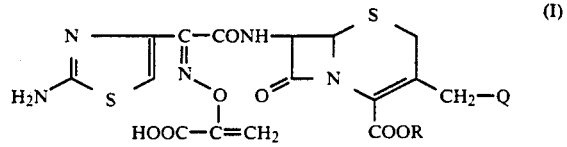

wherein R is a hydrogen atom, a carboxyl-protecting group or a negative charge and Q is a hydrogen atom, a halogen atom, a hydroxyl group, an acetoxy group, a carbamoyloxy group, an azide group, a substituted or unsubstituted quarternary ammonio group or a substituted or unsubstituted heterocyclic thio group having at least one hetero atom selected from the group consisting of a nitrogen atom, an oxygen atom, or a sulfur atom, or a non-toxic salt or physiologically hydrolyzable non-toxic ester thereof, a process for producing it and an antibacterial agent comprising it as an active ingredient.

Further, the present invention provides a compound having the formula III which is an intermediate for producing the compound of the formula I.

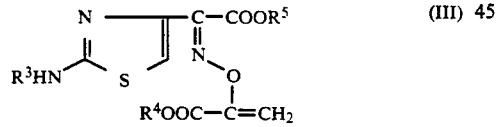

wherein $R^3$ is a hydrogen atom or an amino-protecting group, and each of $R^4$ and $R^5$ which may be the same or different is a hydrogen atom or a carboxyl-protecting group, or a salt thereof and a process for producing it.

Now, the symbols and terms used in the present specification will be explained.

The lower alkyl group is a straight chain, branched chain or cyclic lower alkyl group.

The straight chain or branched chain lower alkyl group is an alkyl group having from 1 to 6 carbon atoms. Specifically, a methyl group, an ethyl group, a n-propyl group, an isopropyl group, a n-butyl group, an isobutyl group, a sec-butyl group, a tert-butyl group, a n-pentyl group or a n-hexyl group may be mentioned. A methyl group, an ethyl group, a n-propyl group or an isopropyl group is particularly preferred.

The cyclic lower alkyl group is a cyclic alkyl group having from 3 to 6 carbon atoms. Specifically, a cyclopropyl group, a cyclobutyl group, a cyclopentyl group or a cyclohexyl group may be mentioned. A cyclopropyl group, a cyclobutyl group or a cyclopentyl group is particularly preferred.

The lower alkenyl group is an alkenyl group having from 2 to 6 carbon atoms. Specifically, a vinyl group, an allyl group, an isopropenyl group, a 1,1-dimethylallyl group, a 2-butenyl group or a 3-butenyl group may be mentioned.

The lower alkynyl group is an alkynyl group having from 2 to 3 carbon atoms. Specifically, an ethynyl group or a 2-propynyl group may be mentioned.

The lower alkoxy group is an alkoxy group having from 1 to 4 carbon atoms. Specifically, a methoxy group, an ethoxy group, a propoxy group, an isopropoxy group, a butoxy group or an isobutoxy group may be mentioned. A methoxy group or an ethoxy group is particularly preferred.

As the alkanoyloxy group, for example, an acetoxy group, a propionyloxy group or a butyryloxy group may be mentioned. An acetoxy group is particularly preferred.

The lower alkoxycarbonyl group is an alkoxycarbonyl group having from 2 to 5 carbon atoms. Specifically, it may be a methoxycarbonyl group, an ethoxycarbonyl group, a propoxycarbonyl group, an isopropoxycarbonyl group, a butoxycarbonyl group or an isobutoxycarbonyl group. A methoxycarbonyl group or an ethoxycarbonyl group is particularly preferred.

The substituted or unsubstituted amino group represents an amino group and an amino group substituted by an alkyl group having from 1 to 4 carbon atoms, for example, an alkylamino group such as a methylamino group, an ethylamino group, a dimethylamino group or an N-ethylmethylamino group, a formylamino group or an alkanoylamino group such as an acetylamino group, a propionylamino group or a butyrylamino group. An amino group, a methylamino group, a dimethylamino group, a formylamino group or an acetylamino group is particularly preferred.

The substituted imino group represents a hydroxyimino group, an imino group substituted by an alkoxy group having from 1 to 4 carbon atoms, for example, an alkoxyimino group such as a methoxyimino group, an ethoxyimino group or a propoxyimino group, or a carboxymethoxyimino group. A hydroxyimino group, a methoxyimino group or a carboxymethoxyimino group is particularly preferred.

The fluoroalkyl group represents a fluorine-substituted alkyl group having from 1 to 4 carbon atoms such as a fluoromethyl group, a trifluoromethyl group or a 2-fluoroethyl group. A trifluoromethyl group or a 2-fluoroethyl group is particularly preferred.

The aryl group represents an aryl group having from 6 to 12 carbon atoms such as a phenyl group or a naphthyl group. A phenyl group is particularly preferred. As the heterocyclic group having at least one hetero atom selected from the group consisting of a nitrogen atom, an oxygen atom and a sulfur atom, there may be mentioned, for example, a thienyl group, a furyl group, an imidazolyl group, a pyrazolyl group, a thiazolyl group, an isothiazolyl group, an oxazolyl group, an isooxazolyl group, a triazolyl group, a thiadiazolyl group, an oxadiazolyl group, a tetrazolyl group, a pyridyl group, a pyrazinyl group, a pyridazinyl group or a triazinyl group. An oxazolyl group, a thiazolyl group, an oxadiazolyl group, a thiadiazolyl group or a tetrazolyl group is particularly preferred.

The halogen atom is a fluorine atom, a chlorine atom, a bromine atom or an iodine atom.

The substituted or unsubstituted quaternary ammonio group is a quaternary ammonio group which has been known as the substituent at the 3-position of the cephem nucleus. Preferred is a substituted or unsubstituted quaternary ammonio group having the formula:

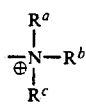

wherein each of $R^a$, $R^b$ and $R^c$ which may be the same or different is a lower alkyl group, a lower alkenyl group or a lower alkynyl group, or two or three of R, R and R bond each other, and together with the adjacent nitrogen atom, form a saturated or unsaturated monocyclic, polycyclic or cross-linked polycyclic group which may contain at least one hetero atom selected from the group consisting of an oxygen atom, a nitrogen atom or a sulfur atom, wherein each of said lower alkyl, lower alkenyl, lower alkynyl, monocyclic, polycyclic and cross-linked polycyclic group may be substituted by one or more substituents which may be the same or different, selected from the group consisting of a hydroxyl group, a lower alkoxy group, a formyloxy group, an alkanoyloxy group, a carbamoyloxy group, a hydroxy lower alkyl group, a sulfo lower alkyl group, a carboxy lower alkyl group, a carbamoyl lower alkyl group, a carboxyl group, a lower alkoxycarbonyl group, a carbamoyl group, a cyano group, a sulfo group, a sulfamoyl group, a substituted or unsubstituted amino group, a halogen atom, an aryl group and a nitrogen atom, an oxygen atom and a sulfur atom, provided that each of said aryl and aromatic heterocylic groups may have one or more substituents which may be the same or different, selected from the group consisting of a lower alkyl group, a lower alkenyl group, a lower alkynyl group, a fluoroalkyl group, a lower alkoxy group, an alkanoyloxy group, a carbamoyloxy group, a carboxyl group, a lower alkoxycarbonyl group, a carbamoyl group, a cyano group, a sulfo group, a sulfamoyl group, a substituted or unsubstituted amino group, a substituted oxyimino group and a halogen atom.

The saturated or unsaturated monocyclic, polycyclic or cross-linked polycyclic group which may contain at least one hetero atom selected from the group consisting of an oxygen atom, a nitrogen atom and a sulfur atom, which may be formed by two or two of said R, R and R together with the adjacent nitrogen atom, includes, for example, an azetidinio group, a pyrrolidinio group, a piperidinio group, a 3-oxopiperidinio group, a 4-oxopiperidinio group, a 1,2,3,6-tetrahydropiperidinio group, a hexamethyleneiminio group, a morpholinio group, a thiomorpholinio group, a 3-oxomorpholinio group, a piperadinio group, a homopiperadinio group, a 3-oxopiperadinio group, an isoindolinio group, a 1,2,3,4-tetrahydroisoquinolinio group, a 2,3,4,5-tetrahydro-1H-2-benzazepinio group, a 1,2,4,5-tetrahydro-3H-3-benzazepinio group, an imidazolinio group, a pyrimidinio group, an oxazolinio group, a pyridazinio group, a thiazolinio group, a pyridinio group, a quinolinio group, an isoquinolinio group, a 1H-imidazo[4,5-b]pyridinio group, a thiazolo[4,5-b]pyridinio group, an oxazo[4,5-b]pyridinio group, a 1H-2-methylimidazo[4,5-b]pyridinio group, a 3-methyl-3H-imidazo[4,5-b]pyridinio group, a 1-methyl-1H-imidazolo[4,5-c]pyridinio group, a 1-methyl-1H-imidazolo[4,5-c]pyridinio group, a 5-aminoisoquinolinio group, a 5-hydroxyisoquinolinio group, a 6-acetoxyisoquinolinio group, a 5,6-diacetoxyisoindolinio group, a 5,6-dihydroxyisoindolinio group, a 4-carboxypyridinio group, a 4-sulfopyridinio group, a 4-carbamoylpyridinio group, a 4-(oxazol-2-yl)pyridinio group, a 4-(4,5-dihydrooxazol-2-yl)pyridinio group, a 2,3-cyclopentenopyridinio group, a 3,4-cyclopentenopyridinio group, a 3,4-cyclohexenopyridinio group, a 3-aminopyridinio group, a 4-(2-carboxyethyl)pyridinio group, a 4-sulfomethylpyridinio group, a 4-(2-sulfoethyl)pyridinio group, a 3-formamidopyridinio group, a 3-acetamidopyridinio group, a 2-hydroxymethylpyridinio group, a dihydrofuranopyridinio group, a 3-hydroxymethylpyridinio group, a 4-hydroxymethylpyridinio group, a 4-(2-hydroxyethyl)pyridinio group, a 3-carboxypyridinio group, a 4-carboxypyridinio group, a 3-carboxymethylpyridinio group, a 3-(2-carboxyethyl)pyridinio group, a 3-carbamoylpyridinio group, a 3-carbamoylmethylpyridinio group, a 3-(2-carbamoylethyl)pyridinio group, a 4-(2-carbamoylethyl)pyridinio group, a 3-fluoropyridinio group, a 4-fluoropyridinio group, a 3-chloropyridinio group, a 4-chloropyridinio group, a 3-bromopyridinio group, a 4-bromopyridinio group, a 3-trifluoromethylpyridinio group, a 4-trifluoromethylpyridinio group, a 4-(2-fluoroethyl)pyridinio group, a sulfamoylpyridinio group, a 1-azoniabicyclo[2.2.1]pentan-1-yl group, a 1-azoniabicyclo[3.3.1]nonan-1-yl group, a quinuclidinio group and a 2-dehydroquinuclidinio group.

The substituted or unsubstituted heterocyclic thio group having at least one hetero atom selected from the group consisting of a nitrogen atom, an oxygen atom or a sulfur atom, includes, for example, a substituted or unsubstituted thienylthio, furylthio, imidazolylthio, pyrazolylthio, thiazolylthio, isothiazolylthio, oxazolylthio, isooxazolylthio, triazolylthio, thiadiazolylthio, oxadiazolylthio, tetrazolylthio, pyridylthio, pyradinylthio, pyridadinylthio and triazinylthio group. The substituent of said heterocyclic thio group is one or more substituents which may be the same or different, selected from the group consisting of a lower alkyl group which may be substituted by, for example, a hydroxyl group, an alkanoyl group, a carbamoyloxy group, a carboxyl group, a carbamoyl group, a cyano group, a sulfo group, a sulfamoyl group, a substituted or unsubstituted amino group, a substituted imino group or a halogen atom, and for example, a lower alkoxy group, a formyloxy group, an alkanoyloxy group, a carbamoyloxy group, a fluoroalkyl group, an alkylidene group of the formula $-(CH_2)_{3-5}-$, a carboxyl group, a lower alkoxycarbonyl group, a carbamoyl group, a cyano group, a sulfo group, a sulfamoyl group, a substituted or unsubstituted amino group, a substituted imino group, a halogen atom, an aryl group and a heterocyclic group having at least one hetero atom selected from the group consisting of a nitrogen atom, an oxygen atom and a sulfur atom. However, each of said aryl and heterocyclic groups may have one or more substituents which may be the same or different, selected from the group consisting of a lower alkyl group, a lower alkenyl group, a lower alkynyl group, a fluoroalkyl group, a hydroxyl group, a lower alkoxy group, an alkanoyloxy group, a carbamoyloxy group, a carboxyl group, a lower alkoxycarbonyl group, a carbamoyl group, a cyano group, a sulfo group, a sulfamoyl group, a substituted or unsubstituted amino group, a substituted oxyimino group, a halogen atom.

Further, said heterocyclic thio group may be condensed with a benzene nucleus. For example, a 2-benzoxazolylthio group, a 2-benzothiazolylthio group or a 2-benzoimidazolylthio group may be mentioned.

Said benzene nucleus may have a substituent. For example, the said benzene nucleus may have one or more substituents which may be the same or different, selected from the group consisting of a lower alkyl group, a hydroxyl group, a fluoroalkyl group, a lower alkoxy group, a formyloxy group, an alkanoyloxy group, a carbamoyloxy group, a fluoroalkyl group, an alkylidene group of the formula —(CH$_2$)$_{3\text{-}5}$—, a carboxyl group, a lower alkoxycarbonyl group, a carbamoyl group, a cyano group, a sulfo group, a sulfamoyl group, a substituted or unsubstituted amino group, a substituted imino group, a halogen atom, an aryl group and a heterocyclic group having at least one hetero atom selected from the group consisting of a nitrogen atom, an oxygen atom and a sulfur atom. However, each of said aryl and heterocyclic groups may have one or more substituents which may be the same or different, selected from the group consisting of a lower alkyl group, a lower alkenyl group, a lower alkynyl group, a fluoroalkyl group, a hydroxyl group, a lower alkoxy group, an alkanoyloxy group, a carbamoyloxy group, a carboxyl group, a lower alkoxycarbonyl group, a carbamoyl group, a cyano group, a sulfo group, a sulfamoyl group, a substituted or unsubstituted amino group, a substituted oxyimino group, a halogen atom.

As the substituted or unsubstituted heterocyclic thio group having at least one hetero atom selected from the group consisting of a nitrogen atom, an oxygen atom and a sulfur atom, there may be mentioned, for example, a (1,3,4-oxazol-2-yl)thiomethyl group, a (5-methyl-1,3,4-oxadiazozol-2-yl)thiomethyl group, a (5-carboxymethyl-1,3,4-oxadiazol-2-yl)thiomethyl group, a [5-(3,4-hydroxyphenyl)-1,3,4-oxadiazole]thiomethyl group, a [5-(3,4-diacetoxyphenyl)-1,3,4-oxadiazole]thiomethyl group, a (5-carboxymethyl-1,3,4-thiadiazol-2-yl)thiomethyl group, a [5-(3,4-dihydroxyphenyl)-1,3,4-thiadiazol-2-yl]thiomethyl group, a 5-(3,4-diacetoxyphenyl)-1,3,4-thiadizol-2-yl]thiomethyl group, a (thiazol-2-yl)thiomethyl group, a (4-methylthiazol-2-yl)thiomethyl group, a (5-carboxymethylthiazol-2-yl)thiomethyl group, a (4-methyl-5-carboxymethylthiazol-2-yl)thiomethyl group, a (4-phenyl-5-carboxymethylthiazol-2-yl)thiomethyl group, a [4-(3,4-dihydroxyphenyl)-5-carboxymethylthiazol-2-yl]thiomethyl group, a [4-(3,4-diacetoxyphenyl)-5-carboxymethylthiazol-2-yl]thiomethyl group, a (4-carboxythiazol-2-yl)thiomethyl group, a [4-carboxy-5-(3,4-dihydorxyphenyl)thiazol-2-yl]thiomethyl group, a [4-carboxy-5-(3,4-diacetoxyphenyl)thiazol-2-yl]thiomethyl group, a (oxazol-2-yl)thiomethyl group, a [5-(3,4-dihydroxyphenyl)oxazol-2-yl]thiomethyl group, a [5-(3,4-diacetoxyphenyl)oxazol-2-yl]thiomethyl group, a (benzoimidazol-2-yl)thiomethyl group, a (1-methylbenzoimidazol-2-yl)thiomethyl group, a (5,6-dihydroxybenzoimidazol-2-yl)thiomethyl group, a (5,6-diacetoxybenzoimidazol-2-yl)thiomethyl group, a (5,6-dihydroxy-1-methylbenzoimidazol-2-yl)thiomethyl group, a (5,6-diacetoxy-1-methylbenzoimidazol-2-yl)thiomethyl group, a benzooxazol-2-yl)thiomethyl group, a (5,6-dihydroxybenzooxazol-2-yl)thiomethyl group, a (5,6-diacetoxybenzooxazol-2-yl)thiomethyl group, a (benzothioazol-2-yl)thiomethyl group, a 5,6-dihydroxybenzothiazol-2-yl)thiomethyl group, a (5,6-diacetoxybenzothiazol-2-yl)thiomethyl group, or the like.

Further, the moiety in the oxyimino group in the formula I, includes a syn-isomer (Z-configuration) and an anti-isomer (E-configuration). Generally, the syn-isomer exhibits superior antibacterial activities. In this specification, the substituted oxyimino group represents the syn-isomer in all cases. The nomenclature for E and Z configurations is given in Journal of the American Chemical Society, Vol. 90, p.509 (1968).

The compounds of the formula I may be converted to non-toxic salts or physiologically hydrolyzable non-toxic esters thereof by usual methods. The non-toxic salts of the compounds of the formula I mean pharmaceutically acceptable usual salts, i.e. salts at the carboxyl group at the 4-position of the cephem nucleus, at the 1-carboxy-1-vinyl group at the 7-position of the cephem nucleus, at the 2-aminothiazole group at the 7-position of the cephem nucleus, and at a carboxyl group or a sulfo group or at the basic residue such as an amino group, which is substituted at Q.

The preferred salts for the formula I include, for example, a salt with a metal such as sodium, potassium, calcium, magnesium or aluminum, a salt with an organic amine such as N,N'-dibenzylethylenediamine or procaine, a salt of an inorganic acid such as hydrochloric acid, hydrobromic acid, nitric acid, sulfuric acid or perchloric acid, a salt with an organic acid such as acetic acid, lactic acid, propionic acid, maleic acid, fumaric acid, maleic acid, tartaric acid or citric acid, a salt with a sulfonic acid such as methanesulfonic acid, isethionic acid or p-toluenesulfonic acid and a salt with an amino acid such as glutamic acid, aspartic acid., lysine or arginine.

The non-toxic-esters of the formula I mean pharmaceutically acceptable usual esters at the carboxyl groups at the 4-position of the cephem nucleus. For example, there may be mentioned an alkanoyloxymethyl group such as an acetoxymethyl group or a pivaloyloxymethyl group, an alkoxycarbonyloxyalkyl group such as a 1-(ethoxycarbonyloxy)ethyl group or a 1-(isopropoxycarbonyloxy)ethyl group, a phthalidyl group or a (5-substituted-2-oxo-1,3-dioxol-4-yl)methyl group such as a (5-methyl-2-oxo-1,3-dioxol-4-yl)methyl group.

It is the feature of the compound of the present invention to have a 1-carboxy-1-vinyloxyimino structure as a moiety for the side chain at the 7-position of the cephem nucleus. There is no particular restriction as to the side chain at the 3-position of the cephem nucleus.

As the side chain at the 3-position of the cephem nucleus, side chains usually used in the field of the cephalosporin chemicals may be exemplified. Typical examples include, for example, a methyl group, a chloromethyl group, a bromomethyl group, an iodomethyl group, a hydroxymethyl group, an acetoxymethyl group, a carbamoyloxy group, an azidomethyl group, a methoxymethyl group, an ethoxymethyl group, a methylthiomethyl group, an ethylthiomethyl group, a (tetrazol-5-yl)thiomethyl group, a (1-methyltetrazol-5-yl)thiomethyl group, a (1-hydroxymethyltetrazol-5-yl)thiomethyl group, a 1-(2-hydroxyethyl)tetrazol-5-yl]thiomethyl group, a (1-carboxymethyltetrazol-5-yl)thiomethyl group, a (1-sulfomethyltetrazol-5-yl)thiomethyl group, a 1-(2-sulfoaminoethyl)tetrazol-5-yl]thiomethyl group, a (1-dimethylaminomethyltetrazol-5-yl)thiomethyl group, a 1-(2-dimethylaminoethyl)tetrazol-5-yl]thiomethyl group, a (1-carboxymethyltetrazol-5-yl)thiomethyl group, a (1,2,3-triazol-4-yl)thiomethyl group, a (3-methyl-1,2,3-triazol-4-yl)thiomethyl group, a (5-methyl-1,2,3-triazol-4-yl)thiomethyl group, a (1,2,4-triazol-5-yl)thiomethyl group, a pyridiniomethyl group, a 2,3-cyclopentenopyridiniomethyl group, a 3,4-cyclopentenopyridiniomethyl group, a 2,3-cyclohexenopyridiniomethyl group, a 3,4-cyclohexenopyridiniomethyl group, a 2,3-dihydrofuro[2,3-b]pyridiniomethyl group, a 2,3-dihydrothieno[2,3-b]pyridiniomethyl group, a 3-aminopyridiniomethyl group, a 3-formamidopyridiniomethyl group, a 3-acetamidopyridiniomethyl group, a 2-hydroxymethylpyridiniomethyl group, a 3-hydroxymethylpyridiniomethyl group, a 4-hydroxymethylpyridiniomethyl group, a 3-(2-hydroxyethyl)pyridiniomethyl group, a 4-(2-hydroxyethyl)pyridiniomethyl group, a 3-carboxypyridiniomethyl group, a 4-carboxypyridiniomethyl group, a 3-carboxymethylpyridiniomethyl group, a 3-(2-carboxyethyl)pyridiniomethyl group, a 4-(2-carboxyethyl)pyridiniomethyl group, a 3-carbamoylpyridiniomethyl group, a 4-carbamoylpyridiniomethyl group, a 3-carbamoylmethylpyridiniomethyl group, a 4-carbamoylmethylpyridiniomethyl group, a 3-(2-carbamoylethyl)pyridiniomethyl group, a 4-(2-carbamoylethyl)pyridiniomethyl group, a 4-sulfomethylpyridiniomethyl group, a 4-(2-sulfoethyl)pyridiniomethyl group, a 3-fluoropyridiniomethyl group, a 4-fluoropyridiniomethyl group, a 3-chloropyridiniomethyl group, a 4-chloropyridiniomethyl group, a 3-bromopyridiniomethyl group, a 4-bromopyridiniomethyl group, a 3-trifluoromethylpyridiniomethyl group, a 4-trifluoromethylpyridiniomethyl group, a [1-(2-dimethylaminoethyl)tetrazol-5-yl]thiomethyl group, a 1,2,3-triazol-5-yl group, a (4-methyl-5-carboxymethylthiazol-2-yl)thiomethyl group, a (3-hydroxy-4-carboxyisothiazol-5-yl)thiomethyl group, a (1-methyl-3-carboxy-1,2,4-triazol-5-yl)thiomethyl group, a (1,2,5,6-tetrahydro-2-methyl-5,6-dioxo-as-triazin-3-yl)thiomethyl group, a (1,2,5,6-tetrahydro-5,6-dioxoas-triazin-3-yl)thiomethyl group, a (2,5-dihydro-5-oxo-2-methyl-as-triazin-3-yl)thiomethyl group, a (2,5-dihydro-6-hydroxy-2-methyl-5-oxoas-triazin-3-yl)thiomethyl group, a (2,5-hydroxy-2-methyl-5-oxo-6-methoxy-as-triazin-3-yl)thiomethyl group, a (5-methyl-1,3,4-thiadiazol-2-yl)thiomethyl group, a (1,3,4-thiadiazol-2-yl)thiomethyl group, a 4-ethoxycarbonyl-1-methyl-1-piperadiniomethyl group, a 1-methyl-1-hexamethyleneiminiomethyl group, a 1,4-dimethyl-1-piperadiniomethyl group, a 1-methyl-1,2,3,6-tetrahydropyridiniomethyl group, a 4-acetyl-1-methylpiperadiniomethyl group, a 3-(1,2,4-oxodiazol-3-yl)pyridiniomethyl group, a 3-(imidazol-2-yl)pyridiniomethyl group, a 1-methylpyrrolidiniomethyl group, a 2-methylisoindoliniomethyl group, a 2-methyl-5,6-dihydroxyisoindoliniomethyl group, a 2-methyl-5,6-diacetoxyisoindoliniomethyl group, a 2-methyl-6,7-dihydroxy-1,2,3,4-tetrahydroisoquinoliniomethyl group, an isoquinolinio group, a quinoliniomethyl group, a 6,7-dihydroxyquinolinio group and a 6,7-diacetoxyquinolinio group.

The preferred examples of the compound of the formula I provided by the present invention, are as follows:

1) 7β-[2-(2-aminothiazol-4-yl)-2-(1-carboxy-1-vinyloxyimino)acetamido]-3-(1,2,3-thiadiazol-5-yl)thiomethyl-3-cephem-4-carboxylic acid (syn-isomer)

2) 7β-[2-(2-aminothiazol-4-yl)-2-(1-carboxy-1-vinyloxyimino)acetamido]-3-carbamoyloxymethyl-3-cephem-4-carboxylic acid (syn-isomer)

3) 7β-[2-(2-aminothiazol-4-yl) 2-(1-carboxyl-1-vinyloxyimino)acetamido]-3-(4-methyl-5-carboxymethylthiazol-2-yl)thiomethyl-3-cephem-4-carboxylic acid (syn-isomer)

4) 7β-8-[2-(2-aminothiazol-4-yl)-2-(1-carboxy-1-vinyloxyimino)acetamido]-3-(5-methyl-1,3,4-thiadiazol-2-yl)thiomethyl-3-cephem-4-carboxylic acid (syn-isomer)

5) 7β-[2-(2-aminothiazol-4-yl)-2-(1-carboxy-1-vinyloxyimino)acetamido]-3-[1-(2-dimethylaminoethyl)tetrazol-5-yl]thiomethyl-3-cephem-4-carboxylic acid (syn-isomer)

6) 7β-[2-(2-aminothiazol-4-yl)-2-(1-carboxy-1-vinyloxyimino)acetamido]-3-[5-(3,4-dihydroxyphenyl)-thiazol-2-yl]-3-cephem-4-carboxylic acid (syn-isomer)

7) 7β-[2-(2-aminothiazol-4-yl)-2-(1-carboxy-1-vinyloxyimino)acetamido]-3-[4-(3,4-diacetoxyphenyl)-5-carboxymethylthiazol-2-yl]thiomethyl-3-cephem-4-carboxylic acid (syn-isomer)

8) 7β-[2-(2-aminothiazol-4-yl)-2-(1-carboxy-1-vinyloxyimino)acetamido]-3-[1-(2-hydroxyethyl)tetrazol-5-yl]thiomethyl-3-cephem-4-carboxylic acid (syn-isomer)

9) 7β-[2-(2-aminothiazol-4-yl)-2-(1-carboxy-1-vinyloxyimino)acetamido]3-(4-carboxy-3-hydroxyisothiazol-5-yl)thiomethyl-3-cephem-4-carboxylic acid (syn-isomer)

10) 7β-[2-(2-aminothiazol-4-yl)-2-(1-carboxy-1-vinyloxyimino)acetamido]-3-(1,2,5,6-tetrahydro-2-methyl-5,6-dioxo-as-triazin-3-yl)thiomethyl-3-cephem-4-carboxylic acid (syn-isomer)

11) 7β-[2-(2-aminothiazol-4-yl)-2-(1-carboxy-1-vinyloxyimino)acetamido]-3-(1-pyridinio)methyl-3-cephem-4-carboxylic acid (syn-isomer)

12) 7β-[2-(2-aminothiazol-4-yl)-2-(1-carboxy-1-vinyloxyimino)acetamido]-3-(2,3-cychlopenteno-1-pyridinio)methyl-3-cephem-4-carboxylic acid (syn-isomer)

13) 7β-[2-(2-aminothiazol-4-yl)-2-(1-carboxy-1-vinyloxyimino)acetamido]-3-(3-carboxy-1-pyridinio)methyl-3-cephem-4-carboxylic acid (syn-isomer)

14) 7β-[2-(2-aminothiazol-4-yl)-2-(1-carboxy-1-vinyloxyimino)acetamido]-3-(3-carbamoyl-1-pyridinio)methyl-3-cephem-4-carboxylic acid (syn-isomer)

15) 7β-[2-(2-aminothiazol-4-yl)-2-(1-carboxy-1-vinyloxyimino)acetamido]-3-(4-carboxy-1-pyridinio)methyl-3-cephem-4-carboxylic acid (syn-isomer)

16) 7β-[2-(2-aminothiazol-4-yl)-2-(1-carboxy-1-vinyloxyimino)acetamido]-3-(4-carbamoyl-1-pyridinio)methyl-3-cephem-4-carboxylic acid (syn-isomer)

17) 7β-[2-(2-aminothiazol-4-yl)-2-(1-carboxy-1-vinyloxyimino)acetamido]-3-(4-sulfonatomethyl-1-pyridinio)methyl-3-cephem-4-carboxylic acid (syn-isomer)

18) 7β-[2-(2-aminothiazol-4-yl)-2-(1-carboxy-1-vinyloxyimino)acetamido]-3-[4-(2-sulfonatoethyl)-1-pyridinio]methyl-3-cephem-4-carboxylic acid (syn-isomer)

19) 7β-[2-(2-aminothiazol-4-yl)-2-(1-carboxy-1-vinyloxyimino)acetamido]-3-(3-amino-1-pyridinio)methyl-3-cephem-4-carboxylic acid (syn-isomer)

20) 7β-[2-(2-aminothiazol-4-yl)-2-(1-carboxy-1-vinyloxyimino)acetamido]-3-(3-formylamino-1-pyridinio)-methyl-3-cephem-4-carboxylic acid (syn-isomer)

21) 7β-[2-(2-aminothiazol-4-yl)-2-(1-carboxy-1-vinyloxyimino)acetamido]-3-[5-(3,4-dihydroxyphenyl)-1,3,4- oxadiazol-2-yl]thiomethyl-3-cephem-4-carboxylic acid (syn-isomer)

22) 7β-[2-(2-aminothiazol-4-yl)-2-(1-carboxy-1-vinyloxyimino)acetamido]-3-[5-(3,4-dihydroxyphenyl)-thiadiazol-2-yl]thiomethyl-3-cephem-4-carboxylic acid (syn-isomer)

7β-[2-(2-aminothiazol-4-yl)-2-(1-carboxy-1-vinyloxyimino)acetamido]-3-[5-(3,4-dihydroxyphenyl)-1,3,4-oxazol-2-yl]thiomethyl-3-cephem-4-carboxylic acid (syn-isomer)

7β-[2-(2-aminothiazol-4-yl)-2-(1-carboxy-1-vinyloxyimino)acetamido]-3-[5-(3,4-dihydroxyphenyl)oxazol-2-yl]thiomethyl-3-cephem-4-carboxylic acid (syn-isomer)

25) 7β-[2-(2-aminothiazol-4-yl)-2-(1-carboxy-1-vinyloxyimino)acetamido]-3-[4-carboxy-5-(3,4-dihydroxyphenyl)thiazol-2-yl]thiomethyl-3-cephem-4-carboxylic acid (syn-isomer)

26) 3-[4-(3,4-diacetoxyphenyl)-5-carboxymethylthiazol-2-yl]thiomethyl-7β-[2-(2-aminothiazol-4-yl)-2-(1-carboxy-1-vinyloxyimino)acetamido]-3-cephem-4-carboxylic acid (syn-isomer)

27) 7β-[2-(2-aminothiazol-4-yl)-2-(1-carboxy-1-vinyloxyimino)acetamido]cephalosporanic acid (syn-isomer)

28) 7β-[2-(2-aminothiazol-4-yl)-2-(1-carboxy-1-vinyloxyimino)acetamido]-3-[5-methyl-1,3,4-oxadiazol-2-yl)thiomethyl-3-cephem-4-carboxylic acid (syn-isomer)

29) 7B- 2-(2-aminothiazol-4-yl)-2-(1-carboxy-1-vinyloxyimino)acetamido]-3-(1-methyltetrazol-5-yl)thiomethyl-3-cephem-4-carboxylic acid (syn-isomer)

30) 7B-[2-(2-aminothiazol-4-yl)-2-(1-carboxy-1-vinyloxyimino)acetamido]-3-(1-carboxymethyl tetrazol-5yl)-thiomethyl-3-cephem-4-carboxylic acid (syn-isomer)

The moiety in the oxyimino group in the formula III, includes a syn-isomer (Z-configuration) and an anti-isomer (E-configuration). In this specification, the substituted oxyimino group is preferably the syn-isomer. However, said syn-isomer may include a small amount of the anti-isomer. The preferred examples of the compound of the formula III provided by the present invention, are as follows:

1) 2-(aminothiazol-4-yl)-2-(1-carboxy-1-vinyloxyimino)acetic acid 2) 2-(aminothiazol-4-yl)-2-(1-tert-butoxycarbonyl-1-vinyloxyimino)acetic acid 3) 2-(2-tert-butoxycarbonylaminothiazol-4-yl)-2-(1-tert-butoxycarbonyl-1-vinyloxyimino)acetic acid 4) 2-(1 tert-butoxycarbonyl-1-vinyloxyimino)-2-(2-formamidothiazol-4-yl)acetic acid 5) 2-(1-tert-butoxycarbonyl-1-vinyloxyimino)-2-(2-tritylaminothiazol-4-yl)acetic acid 6) 2-(1-tert-butoxycarbonyl-1-vinyloxyimino)-2-(2-chloroacetamidothiazol-4-yl)acetic acid 7) 2-(aminothiazol-4-yl)-2-(1-benzhydryloxycarbonyl-1-vinyloxyimino)acetic acid 8) 2-(1-benzhydryloxycarbonyl-1-vinyloxyimino)-2-(2-tert-butoxycarbonylaminothiazol-4-yl)acetic acid 9) 2-(1-benzhydryloxycarbonyl-1-vinyloxyimino)-2-(2-formamidothiazol-4-yl)acetic acid 10) 2-(1-benzhydryloxycarbonyl-1-vinyloxyimino)-2-(2-tritylaminothiazol-4-yl)acetic acid 11) 2-(1-benzhydryloxycarbonyl-1-vinyloxyimino)-2-(2-chloroacetamidothiazol-4-yl)acetic acid 12) Methyl 2-(aminothiazol-4-yl)-2-(1-tertbutoxycarbonyl-1-vinyloxyimino)acetate 13) Methyl 2-(2-tert-butoxycarbonylaminothiazol-4-yl)-2-(1-tert-butoxycarbonyl-1-vinyloxyimino)acetate 14) Methyl 2-(1-tert-butoxycarbonyl-1-vinyloxyimino)-2-(formamidothiazol-4-yl)acetate 15) Methyl 2-(1-tert-butoxycarbonyl-1-vinyloxyimino)-2-(2-tritylaminothiazol-4-yl)acetate 16) Methyl 2-(1-tert-butoxycarbonyl-1-vinyloxyimino)-2-(2-chloroacetamidothiazol-4-yl)acetate 17) Methyl 2-(aminothiazol-4-yl)-2-(1-benzhydryloxycarbonyl-1-vinyloxyimino)acetate 18) Methyl 2-(1-benzhydryloxycarbonyl-1-vinyloxyimino)-2-(2-tert-butoxycarbonylaminothiazol-4-yl)acetate 19) Methyl 2-(1-benzhydryloxycarbonyl-1-vinyloxyimino)-2-(2-formamidothiazol-4-yl)acetate 20) Methyl 2-(1-benzhydryloxycarbonyl-1-vinyloxyimino)-2-(2-tritylaminothiazol-4-yl)acetate 21) Methyl 2-(1-benzhydryloxycarbonyl-1-vinyloxyimino)-2-(2-chloroacetamidothiazol-4-yl)acetate Now, the process for the preparation of the compounds of the present invention will be described.

The compound of the formula I of the present invention can be prepared by acylating a compound of the formula:

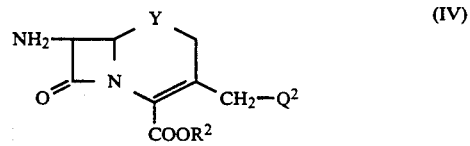

(IV)

wherein $R^2$ is a hydrogen atom, a carboxyl-protecting group or a negative charge, $Q^2$ is a hydrogen atom, a halogen atom, a hydroxy group, an acetoxy group, a carbamoyloxy group, an azide group, a substituted or unsubstituted quarternary ammonio group or a substituted or unsubstituted heterocyclic thio group having at least one hetero atom selected from the group consisting of a nitrogen atom, an oxygen atom or a sulfur atom, and Y is S or SO, provided that $Q^2$ and substituents thereof may be protected, or a salt thereof, with a carboxylic acid of the formula:

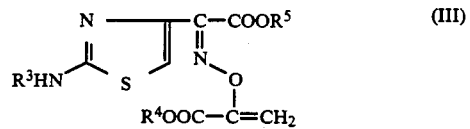

(III)

wherein, $R^3$ is a hydrogen atom or an amino-protecting group and $R^4$ is a hydrogen atom or a carboxyl-protecting group, or a reactive derivative thereof, to form a compound having the formula:

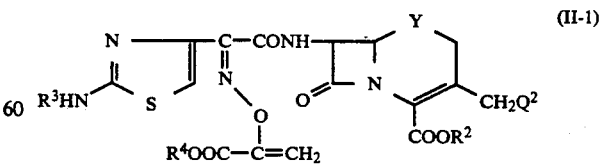

(II-1)

wherein $R^2$, $R^3$, $R^4$, $Q^2$ and Y are as defined above, or a salt thereof, and, if necessary, reacting a nucleophilic agent to the compound of the formula II-1 wherein $Q^2$ is a leaving group, or a salt thereof to form a compound having the formula:

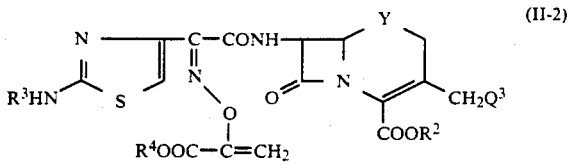

wherein $R^2$, $R^3$, $R^4$ and Y are as defined above and $Q^3$ is a halogen atom, a hydroxyl group, a carbamoyloxy group, an azide group, a substituted or unsubstituted quarternary ammonio group or a substituted or unsubstituted heterocyclic thio group having at least one hetero atom selected from the group consisting of a nitrogen atom, an oxygen atom or a sulfur atom, or a salt thereof, and then, if necessary, reducing the compound of the formula II-1 or II-2, or a salt thereof and/or removing the protecting group from the compound of the formula II-1 or II-2, or a salt thereof.

When $Q^2$ is a leaving group in the compound of the formula II-1, as such a leaving group, there may be specifically mentioned a halogen atom such as chlorine, bromine or iodine, an acetoxy group or a carbamoyloxy group. A chlorine atom, a bromine atom, an iodine atom or an acetoxy group is particularly preferred.

Further, the nucleophilic agent reacting with the compound of the formula II-1 includes all nucleophilic agents usually used in the field of the cephalosporin chemicals.

As the nitrogen nucleophilic agent, there may be mentioned, for example, a tertiary aliphatic amine derivative, an aromatic amine derivative, an aromatic aliphatic amine derivative or a cyclic amine derivative, as well as a pyrimidine, purine, pyridazine, pyrazine, pyrazole, imidazole or triazole derivative which has at least one different hetero atom or an azide derivative.

As the sulfur nucleophilic agent, there may be mentioned a dithiocarbamate derivative, an aromatic thioamide derivative, an aliphatic thioamide derivative, a cyclic thioamide derivative, a thiosulfate derivative, a thiol derivative, a thiophenol derivative or a thio acid derivative. As such nucleophilic reagents, commercially readily available ones can usually be used.

The mercapto derivative having the adjacent two hydroxyl or acetoxy groups, which provides the compound of the present invention, is a novel compound not disclosed in any literature. The compound can be produced by the following methods.

A 2-mercapto-5-(3,4-disubstituted phenyl)-1,3,4-oxadiazole derivative can be prepared by reacting a benzohydrazide derivative with carbon disulfide in an ethanol solvent in the presence of potassium hydroxide.

A 2-mercapto-5-(3,4-disubstituted phenyl)-1,3,4-thiadiazole derivative can be prepared by the following method i or ii.

(i) It can be prepared by reacting a 3,4-disubstituted thiobenzamide with hydrogen sulfide in a pyridine solvent in the presence of triethylamine.

(ii) It can be prepared by reacting a potassium 3-(3,4-disubstituted benzoyl)dithiocarbazate with concentrated sulfuric acid.

A 2-mercapto-4-(3,4-disubstituted phenyl)thiazole derivative can be prepared by reacting 2-chloro-3',4'-dihydroxyacetophenone which is prepared in accordance with the method disclosed in Chemical Abstracts, 84-43639s (1976), with ammonium dithiocarbamate in a methanol solvent.

A 4-carboxy-5-(3,4-disubstituted phenyl)-2-mercaptothiazole derivative can be prepared by converting piperonal as a starting material in accordance with the method disclosed in Organic Syntheses, Coll. Voll., II, p.11–12, 1–3 and 519–520, to a 3-(3,4-disubstituted phenyl)pyruvic acid, brominating the compound to obtain a 3-bromo-(3,4-disubstituted phenyl)pyruvic acid, and further reacting ammonium dithiocarbamate the compound.

A 5-carboxymethyl-2-mercaptothiazole derivative can be prepared by reacting veratrole with succinic anhydride in the presence of anhydrous aluminum chloride to obtain 3-(3,4-dimethoxybenzoyl)propionic acid, subjecting the compound to demethylation with hydrobromic acid to obtain 3-(3,4-dihydroxybenzoyl)propionic acid, subjecting the compound to enol-lactonation in the presence of acetic anhydride and sodium acetate, reacting the resulting compound sequentially with N-bromosuccinimide and with diphenyldiazomethane to obtain 3-(3,4-diacetoxybenzoyl)-3-bromopropionate, and further reacting the compound with ammonium dithiocarbamate.

A 2-mercapto-5-(3,4-disubstituted phenyl)oxazole derivative can be prepared by reacting 2-chloro-3',4'-dihydroxyacetophenone prepared in accordance with the method disclosed in Chemical Abstract, 84-43639s (1976), with sodium azide to obtain an azide compound, conducting catalytic reduction of the compound to convert it to 2-amino-3',4'-dihydroxyacetophenone, and further reacting the compound with carbon disulfide in an ethanol solvent in the presence of sodium ethoxide in accordance with the method disclosed in Chemical Abstracts, 67-43806t (1967).

A 2-mercaptobenzoimidazole derivative can be prepared by using veratrole as a starting material in accordance with the methods disclosed in Synthesis, p.1033 (1974) and in Organic Syntheses, Coll. Voll., IV, p.56 (1963).

A 2-mercaptobenzooxazole derivative can be prepared by using veratraldehyde as a starting material in accordance with the methods disclosed in Journal of the Chemical Society Perkin Transactions 1, p.1353 (1974), Canadian Journal of Chemistry, Vol. 44, p.1879 (1966) and Journal of Pharmaceutical Science, Vol. 76, p.1002 (1956). A 2-mercaptobenzothiazole derivative can be prepared by conducting nitration and catalytic reduction by using veratrole as a starting material, to obtain 3,4-dimethoxy-6-nitroaniline, converting the compound to a diazonium salt, then, reacting the diazonium salt with potassium O-ethyl dithiocarbonate to obtain O-ethyl S-(3,4-dimethoxy-6-nitrophenyl) dithiocarbonate, and further conducting a reductive ring closure reaction with stannous chloride in an ethanol solvent.

Now, the process for the preparation of the compound of the formula I of the present invention, will be described in detail.

The compound of the formula II-1 can be prepared by reacting the compound of the formula IV with the carboxylic acid of the formula III or its reactive derivative (such as its acid halide, mixed anhydride or activated ester). The reaction is conducted in a solvent inert to the reaction such as water, acetone, dioxane, acetonitrile, tetrahydrofuran, methylene chloride, chloroform, ethylene chloride, benzene, ethyl acetate, N,N-dimethylformamide or dimethylsulfxide, or in a mixture of such solvents by using from 1 to 1.5 mols of the carboxylic acid of the formula III or its reactive derivative relative to 1 mol of the compound of the formula IV, and the reaction temperature is from −40° to 40° C.

When an acid halide is used as the reactive derivative of the formula III, the reaction is preferably conducted in the presence of an acid-absorbing agent such as triethylamine, N-methylmorpholine, N,N-diemthylaniline or pyridine.

The acid halide-forming reaction is carried out by using from 1 to 10 mols, preferably from 1 to 1.5 mols of the halogenating agent such as thionyl chloride, phosphorus trichloride, phosphorus tribromide, phosphorus pentachloride, phosphorus oxychloride, oxalylchloride or phosgene, relative to 1 mol of the carboxylic acid of the formula III, at a reaction temperature of from −40° to 100°, preferably from −20° to 20°, and the reaction is completed for from 10 to 120 minutes.

The mixed acid anhydride-forming reaction is conducted by using from 1 to 1.2 mols of a chloroformate such as methyl chloroformate, ethyl chloroformate or isobutyl chloroformate in the presence of from 1 to 1.2 mols of an acid-absorbing agent such as triethylamine, N-methylmorpholine, N,N-dimethylaniline or pyridine, relative to 1 mol of the carboxylic acid of the formula III. The reaction temperature is from −40° to 20° C., preferably from −0° to 5° C. The reaction time is from 10 to 60 minutes.

The active ester-forming reaction is conducted by using from 1 to 1.2 mols of a N-hydroxy compound (such as N-hydroxysuccinimide or 1-hydroxybenzotriazole) or a phenol compound (such as 4-nitrophenol, 2,4-dinitrophenol or 2,4,5-trichlorophenol) and from 1 to 1.4 mols of N,N'-dicychlohexylcarbodiimide, relative to 1 mol of the carboxylic acid of the formula III. The reaction temperature is from −10° to 50° C. The reaction time is from 0.5 to 2 hours.

When the carboxylic acid of the formula III is used in the form of a free acid in the acylation reaction, the compound of the formula II-1 may be prepared in the presence of a condensation agent, for example, a carbodiimide such as N,N'-dicychlohexylcarbodiimide, phosphorus oxychloride, or a phosphorus oxychloride adduct of N,N-dimethylformamide.

Further, when $Q^2$ in the formula II-1 is a leaving group, the leaving group is optionally subjected to substitution reaction by a nucleophilic reagent. The substitution reaction can be conducted in water or an organic solvent such as methylene chloride, chloroform, diethyl ether, ethyl acetate, butyl acetate, tetrahydrofuran, acetonitrile, N,N-dimethylformamide or dimethylsulfoxide, or in a mixture of such solvents.

The reaction is conducted by using from 1 to 2 mols of such a nucleophilic reagent relative to one mol of the compound of the formula II-1 at a reaction temperature of from −20° to 40° C. for a reaction time of from 0.5 to 5 hours.

Further, when $Q^2$ in the formula II-1 is an acetoxy group, the reaction with said nucleophilic agent can be conducted in water, a phosphate buffer or an organic solvent such as acetone, acetonitrile, methanol, ethanol, tetrahydrofuran, acetonitrile, N,N-dimethylformamide or dimethylsulfoxide, or in a mixture of such solvents. The reaction is preferably conducted under a nearly neutral condition. The reaction temperature is from room temperature to 90° C., and the reaction time is from 1 to 15 hours. This reaction is facilitated by conducting it in the presence of an iodide compound such as sodium iodide or potassium iodide, a thiocyanate such as sodium thiocyanate or potassium thiocyanate, and a quaternary ammonium salt such as trimethylbenzylammonium bromide.

The sulfoxide group of the compound of the formula II-1 or II-2 wherein group Y is SO, can be reduced in accordance with the methods disclosed in Journal of Organic Chemistry, Vol. 35, p.2430 (1974) and the like. For example, it may be mentioned that the compound of the formula II-1 or II-2 wherein group Y is SO can be reduced by phosphorus trichloride or acetyl chloride/sodium iodide. Namely, the compound of the formula II-1 or II-2 wherein group Y is SO, can be reduced by reacting it with phosphorus trichloride in a solvent such as N,N-diemthylformamide at a temperature of from −40° to 0° C. for from 1 to 5 hours. The reaction is conducted by using from 2 to 6 mols of phosphorus trichloride relative to one mol of the compound of the formula II-1 or II-2.

Or, the compound of the formula II-1 or II-2 wherein group Y is SO, can be reduced by a dropwise addition of acetyl chloride in an acetone solvent in the presence of sodium iodide or an idodide compound at a temperature of from −40° to 0° C. for from 1 to 5 hours for reaction. The reaction is conducted by using from 3.5 to 10 mols of an iodide compound and from 1.2 to 5 mols of acetyl chloride relative to one mol of the compound of the formula II-1 or II-2 wherein group Y is SO. The compound of the formula I of the present invention can be prepared by optionally removing the protecting group from the compound of the formula II-1 or II-2 wherein group Y is S.

As the protecting groups for the carboxyl, amino and hydroxyl groups in the above formulas, protecting groups which are commonly employed in the field of β-lactam synthesis, may suitably be selected. The introduction and removal of the protecting groups may be conducted in accordance with the methods disclosed in, for instance, "Protective Groups in Organic Synthesis" written by T. W. Greene published in 1981 by Wiley Company and in "Protective Groups in Organic Chemistry" written by J. F. W. McOmie published in 1973 by Plenuum Press.

As the carboxyl-protecting group, there may be mentioned, for example, a tert-butyl group, a 2,2,2-trichloroethyl group, an acetoxymethyl group, a propionyloxymethyl group, a pivaloyloxymethyl group, a 1-acetoxyethyl group, a 1-propionyloxyethyl group, a 1-(ethoxycarbonyloxy)ethyl group, a phthalidyl group, a benzyl group, a 4-methoxybenzyl group, a 3,4-dimethoxybenzyl group, a 4-nitrobenzyl group, a benzhydryl group, a bis(4-methoxyphenyl)methyl group, a (5-methyl-2-oxo-1,3-dioxol-4-yl)methyl group, a trimethylsilyl group or a tert-butyldimethylsilyl group. Particularly preferred are a benzhydryl group, a tert-butyl group and a silyl group.

As the amino-protecting group, there may be mentioned, for example, a trityl group, a formyl group, a chloroacetyl group, a trifluoroacetyl group, a tert-butoxycarbonyl group, a trimethylsilyl group or a tert-butyldimethylsilyl group.

As the hydroxyl-protecting group, there may be mentioned, for example, a 2-methoxyethoxymethyl group, a methoxymethyl group, a methylthiomethyl group, a tetrahydropyranyl group, a phenacyl group, an isopropyl group, a tert-butyl group, a benzyl group, a 4-nitrobenzyl group, an acetyl group, a 2,2,2-trichloroethoxycarbonyl group, a benzyloxycarbonyl group, a trimethylsilyl group or a tert-butyldimethylsilyl group, or a cyclic acetal such as methylene acetal, ethylene acetal or benzylidene acetal, an orthoester such as methoxymethylidene or methoxyethylidene, a cyclic ketal such as isopropylidene ketal or a cyclic carbonate, which is formed by the combination of protecting groups each other.

The removal of the protecting group may be conducted by employing a suitable method selected from usual methods depending upon the type of the protecting group. For instance, the removal of a protecting group such as a trityl group, a formyl group, a tert-butoxycarbonyl group, a benzhydryl group, a tert-butyl group or a 2-methoxyethoxymethyl group, may be conducted by means of an inorganic or organic acid such as hydrochloric acid, formic acid, trifluoroacetic acid, benzenesulfonic acid or p-toluenesulfonic acid. Trifluoroacetic acid is particularly preferred. When trifluoroacetic acid is used as the acid, the reaction can be facilitated by an addition of anisole, thioanisole or phenol, and side reactions can be thereby suppressed. The reaction may be conducted in a solvent which does not adversely affect the reaction, such as water, methylene chloride, chloroform, ethylene chloride or benzene, or in a mixture of such solvents. The reaction temperature and time are suitably selected depending upon the chemical properties of the compound of the formula II-1 or II-2 and that of the compound of the formula I of the present invention, and the type of the protecting group. The reaction is preferably conducted under a mild condition ranging from an ice-cooling condition to a slightly heated condition.

The compound of the formula IV or II-1 wherein group Y is SO, can be prepared by oxidizing the compound of the formula IV or II-1 wherein group Y is S, with m-chloroperbenzoic acid, hydrogene peroxide or metaperiodic acid in an organic solvent inert to the reaction such as methylene chloride, ethylene chloride, chloroform, diethyl ether or acetic acid at a temperature of from ice-cooling to room temperature (the Journal of Organic Chemistry, Vol. 35, p.2430 (1970)).

The compound of the formula IV wherein group Y is an iodine atom, can be prepared by reacting the compound of the formula II-1 wherein group $Q^2$ is a chlorine atom with an iodide compound such as sodium iodide in a solvent such as acetone or N,N-dimethylformamide at a temperature of from ice-cooling to room temperature (e.g. Japanese Examined Patent Publication No. 27679/1976 or Synthetic Communications, Vol. 16, p.1029-1035 (1986)). The product may be used for the subsequent reaction without or after isolation.

Further, the compound of the formula IV can be prepared in accordance with the methods disclosed in "Cephalosporins and Penicillins", p.151-171 and 675 written by Flynn published in 1972 by Academic Press, "Journal of Organic Chemistry", Vol. 32, p.500 (1967) and Japanese Unexamined Patent Publication No. 154786/1979. For instance, a 7β-amino-3-chloromethyl-3-cephem-4-carboxylic acid derivative (e.g. prepared in accordance with the method disclosed in Japanese Unexamined Patent Publication-2-6 No. 76089/1975 or No. 86178/1981), a 7β-acylamino-3-halomethyl-3-cephem-4-carboxylic acid derivative (e.g. prepared in accordance with the method disclosed in Japanese Unexamined Patent Publication No. 72590/1983 or No. 154588/1983), a 7β-aminocephalosporanic acid or a 7β-acylaminocephalosporanic acid derivative, is reacted with the above nucleophilic reagent to obtain a compound having the formula:

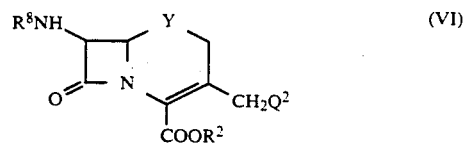

wherein $R^2$ is a hydrogen atom, a carboxyl-protecting group or a negative charge, $R^8$ is a hydrogen atom or an acyl group, $Q^2$ is a hydrogen atom, a halogen atom, a hydroxyl group, an acetoxy group, a carbamoyloxy group, an azide group, a substituted or unsubstituted quarternary ammonio group or a substituted or unsubstituted heterocyclic thio group having at least one hetero atom selected from the group consisting of a nitrogen atom, an oxygen atom or a sulfur atom, and Y is S or SO, provided that $Q^2$ and a substituent thereof may be protected, optionally followed by deacylation.

The deacylation reaction is commonly known in this field. For example, there is a method comprising iminochlorination by phosphorus pentachloride or the like, followed by iminoetherification with methanol or the like and hydrolysis (e.g. Japanese Examined Patent Publication No. 20319/1974) or a method by an acylase (e.g. Japanese Examined Patent Publication No. 291431/1986).

As an acyl group, for example, a phenylacetyl group, a phenoxyacetyl group or an aminoadipyl group may be mentioned.

Now, the process for producing the compound of the formula III which is the second object of the present invention, which is useful as an intermediary material of the compound of the present invention, will be explained.

The compound of the formula III can be prepared by reacting a compound having the formula:

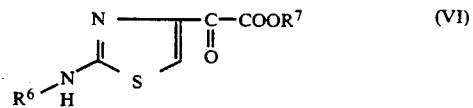

wherein $R^6$ is a hydrogen atom or an amino-protecting group and $R^7$ is a hydrogen atom or a carboxyl-protecting group, with a compound having the formula:

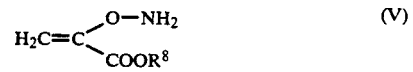

wherein $R^8$ is a hydrogen atom or a carboxyl-protecting group, optionally followed by removal of the protecting groups.

The reaction of the compound of the formula VI with the hydroxylamine derivative of the formula V, is conducted by using from 1.0 to 1.5 mols of the compound of the formula V relative to one mol of the compound of the formula VI in a suitable solvent which does not adversely affect the reaction, such as water, methanol, ethanol, tetrahydrofuran, N,N-dimethylformamide or dimethylsulfoxide, or a mixture of such an organic solvent with water, at a reaction temperature of from 5° to 70° C. for a reaction time of from 0.5 to 5 hours, whereby the reaction is completed.

After completion of the reaction, if necessary, the removal of the protecting groups of the compound of the present invention may be conducted by employing a suitable method selected from those usually used in the field of the organic synthesis chemistry. The removal of the protecting group can be conducted in accordance with a method disclosed in e.g. "Protective Groups in Organic Synthesis", written by T. W. Green published in 1981 by Wiley Company or in "Protective Groups in Organic Chemistry" written by J. F. W. McOmie published in 1973 by Plenum Press. Particularly preferred protecting group is one which can readily be removed by a usual method such as acid treatment, hydrolysis or reduction.

For instance, when the amino-protecting group for $R^6$ is a formyl group, a benzhydryl group, a trityl group or a tert-butoxycarbonyl group, and/or each of the carboxyl-protecting groups for $R^7$ and $R^8$ which may be the same or different is a tert-butyl group or a benzhydryl group, the protecting group can be removed by treating the compound of the formula III of the present invention with an inorganic or organic acid such as hydrochloric acid, formic acid, trifluoroacetic acid, benzenesulfonic acid or p-toluenesulfonic acid. Particularly preferred is trifluoroacetic acid. When trifluoroacetic acid is used as the acid, the reaction can be facilitated by an addition of anisole, thioanisole or phenol, and side reactions can be thereby suppressed. The reaction may be conducted by using from 0.1 to 20 equivalent times (V/W), preferably from 0.5 to 10 equivalent times (V/W) of the acid relative to one equivalent of the compound of the present invention in a solvent which does not adversely affect the reaction, such as water, methylene chloride, chloroform, ethylene chloride or benzene, or in a mixture of such solvents. The reaction may be conducted under a mild condition ranging from an ice-cooling condition to a slightly heated condition. For instance, when the amino-protecting group for $R^6$ is a trifluoroacethyl group, a trimethylsilyl group, and/or each of the carboxyl-protecting groups for $R^7$ and $R^8$ which may be the same or different, is a methyl group, an ethyl group, a propyl group, an isopropyl group, a tert-butyl group, a benzyl group or benzhydryl group, the protecting group of the compound of the formula III of the present invention can be removed by, for example, hydrolysis with an alkali or an acid. As such an alkali, there may be mentioned an alkali metal hydroxide such as sodium hydroxide or potassium hydroxide, or an alkali metal carbonate such as sodium carbonate or potassium carbonate. As such an acid, for example, hydrochloric acid, hydrobromic acid or diluted sulfuric acid may be mentioned. The reaction is conducted by using from 0.5 to 5 equivalent mol, preferably from 1 to 3 equivalent of the base or from 0.1 to 20 times (V/W) preferably from 0.5 to 10 times (V/W) of the acid relative to one equivalent of the compound of the present invention in a solvent such as water, methanol, ethanol, tetrahydrofuran or dioxane, or in a mixture of such solvents, and the reaction temperature is from 0° to 80° C.

For instance, when the amino-protecting group for $R^6$ is a benzyloxycarbonyl group, and/or each of the carboxyl-protecting groups for $R^7$ and $R^8$ which may be the same or different, is a benzyl group, a 4-methoxybenzyl group, a 3,4-dimethoxybenzyl group, a 4-nitrobenzyl group or a benzhydryl group, the protecting group can be removed by conducting a catalytic reduction of the compound of the formula III of the present invention under a hydrogen gas stream in the presence of a catalyst such as palladium black under an atmospheric pressure to an elevated pressure at a temperature of from 10° to 70° C. As the solvent for the reaction, for example, water, methanol, ethanol or tetrahydrofuran, or a mixture of such organic solvents and water may be employed.

After completion of the reaction, the isolation and purification of the compound of the formula III of the present invention or its salt from the reaction solution, can be conducted by means of a separation method such as extraction with a solvent, recrystallization or chromatography. Further, the compound of the formula III of the present invention can be converted to an addition salt with a base or an acid, or a solvate with a suitable solvent by a usual method.

As the addition salt of the compound of the formula III of the present invention with the base, there may be mentioned a salt of an alkali metal such as sodium or potassium, a salt of an alkali earth metal such as calcium or magnesium, or a salt of an amine such as ammonium, trimethylamine, triethylamine, dicyclohexylamine, N,N'-dibenzylethylenediamine, ethanolamine, diethanolamine, triethanolamine, procaine, pyridine, picoline, quinoline or isoquinoline. Further, as the addition salt with an acid, there may be mentioned a salt of an inorganic acid such as hydrochloric acid, hydrobromic acid, sulfuric acid, nitric acid, phosphoric acid, carbonic acid, hydrogencarbonic acid or perchloric acid, a salt of an organic acid such as acetic acid, propionic acid or trifluoroacetic acid, a salt of a sulfonic acid such as methanesulfonic acid, isethionic acid, benzenesulfonic acid or p-toluenesulfonic acid, or a salt of an amino acid such as arginine or lysine.

As the solvent forming the solvate with the compound of the formula III of the present invention, there may be mentioned, for example, water, methanol, ethanol, propanol, glycol, methylcellosolve, acetone, acetonitrile, tetrahydrofuran, dioxane, benzene, toluene, xylene, methylene chloride, chloroform, carbon tetrachloride, ethylene chloride, formamide, N,N-dimethylformamide, acetamide, N,N-dimethylacetamide or dimethylsulfoxide.

The starting material compound of the formula III of the present invention can be prepared in accordance with the method disclosed, for example, in Journal of the Japanese Chemical Society, p.785–801 (1981).

Further, the starting material compound of the formula VIII is a novel compound and can be prepared in accordance with, for example, the following reaction scheme.

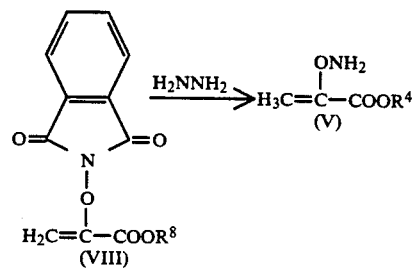

In the formulas, $R^8$ is a hydrogen atom or a carboxyl-protecting group.

Namely, the compound of the formula VII can be prepared by reacting a N-(1-carboxy-1-vinyloxy)phthalimide derivative of the formula VIII obtained in accordance with the method disclosed in the specification of British Patent No. 1,602,725, with hydrazine in an amount of from 1.0 to 2.5 mols relative to one mol of the compound of the formula VIII in a solvent such as methanol, ethanol, methylene chloride, ethylene chloride, tetrahydrofuran, N,N-dimethylformamide or dimethylsulfoxide at a reaction temperature of from $-5°$ to $40°$ C. The product can be used for the subsequent reaction after or without isolation.

Now, the in vitro antibacterial activities of the compounds of the present invention against various microorganisms, were measured by the following agar plate dilution method.

One platinum loopfull of each test microorganism incubated overnight in Mueller Hinton broth, was inoculated to Mueller Hinton agar (MH agaer). Such culture media containing various antibiotics in various concentrations were prepared. After incubation at $37°$ C. for 16 hours, the minimum inhibitory concentrations (MIC: $\mu g/ml$) were measured. The results are shown in the following Table.

| Tested compound Test microorganism (*β-Lactamase-producing strain) | MIC (μg/ml:10⁶ CFU/ml) | | | | | | | | | |
|---|---|---|---|---|---|---|---|---|---|---|
| | Example 1 | Example 2 | Example 3 | Example 4 | Example 5 | Example 6 | Example 7 | Example 8 | Example 9 | Example 10 |
| 1. S. aureus 209P NIHJ-JC1 | 3.12 | 1.56 | 6.25 | 1.56 | 12.5 | 1.56 | 25 | 6.25 | 3.12 | 1.56 |
| 2. E. coli NIHJ JC2 | 0.025 | 0.05 | 0.2 | 0.05 | 0.2 | 0.05 | 0.1 | 0.05 | 0.025 | 0.0125 |
| 3. E. coli CSH2(RK1)* | 0.0125 | 0.025 | 0.05 | 0.025 | 0.2 | 0.025 | 0.2 | 0.05 | 0.025 | 0.0125 |
| 4. K. pneumoniae PCI-602 | <0.006 | 0.0125 | 0.025 | 0.0125 | 0.05 | <0.006 | 0.025 | 0.025 | <0.006 | <0.006 |
| 5. E. coli CSH(RE45)* | 0.025 | 0.78 | 0.05 | 0.025 | 0.39 | 0.025 | 0.05 | 0.05 | 0.0125 | 0.0125 |
| 6. K. oxytoca GN10650* | 0.1 | 0.1 | 0.2 | 0.1 | 0.39 | 0.2 | 0.39 | 0.2 | 0.1 | 0.05 |
| 7. K. pneumoniae No. 42* | 0.1 | 0.39 | 0.39 | 0.1 | 0.39 | 0.1 | 0.1 | 0.39 | 0.1 | 0.05 |
| 8. P. vulgaris HX-19 | 0.0125 | 0.025 | 0.0125 | 0.0125 | <0.006 | 0.0125 | 0.0125 | 0.025 | 0.0125 | <0.006 |
| 9. P. vulgaris No. 33* | 0.0125 | 0.025 | 0.05 | 0.0125 | 0.0125 | <0.006 | 0.0125 | 0.05 | 0.0125 | 0.0125 |
| 10. S. marcescens IAN 1184 | <0.006 | 0.0125 | 0.05 | 0.0125 | 0.025 | <0.006 | 0.0125 | 0.025 | <0.006 | <0.006 |
| 11. E. cloacae 963 | 0.025 | 0.05 | 0.1 | 0.05 | 0.2 | 0.05 | 0.1 | 0.2 | 0.05 | 0.025 |
| 12. E. cloacae Nek 39* | 0.39 | 0.2 | 3.12 | 0.2 | 3.12 | 1.56 | 3.12 | 0.78 | 0.78 | 0.39 |
| 13. E. coli GN5482* | 0.2 | 0.1 | 3.12 | 0.2 | 1.56 | 0.39 | 1.56 | 0.39 | 0.2 | 0.1 |
| 14. M. morganii GN5407* | 0.0125 | 0.025 | 0.05 | 0.0125 | 0.025 | 0.025 | 3.12 | 0.05 | 0.39 | 0.0125 |
| 15. S. marcescens No. 16-2* | 0.78 | 0.78 | 3.12 | 0.78 | 6.25 | 3.12 | 3.12 | 3.12 | 1.56 | 1.56 |
| 16. Ps. aeruginosa IF03445 | 0.78 | 1.56 | 6.25 | 1.56 | 25 | 6.25 | 3.12 | 3.12 | 0.78 | 0.78 |
| 17. Ps. aeruginosa AK 109 | 1.56 | 1.56 | 100 | 12.5 | 25 | 12.5 | 25 | 12.5 | 3.12 | 3.12 |
| 18. Ps. aeruginosa AKR17 | >100 | 100 | >100 | >100 | >100 | >100 | >100 | >100 | >100 | >100 |
| 19. Ps. cepacia 23 | 3.12 | 0.39 | 6.25 | 3.12 | 12.5 | 3.12 | 12.5 | 12.5 | 3.12 | 3.12 |
| 20. A. calcoaceticus No. 4 | 12.5 | 3.12 | 25 | 3.12 | 50 | 12.5 | 50 | 12.5 | 6.25 | 3.12 |

| Tested compound Test microorganism (*β-Lactamase-producing strain) | MIC (μg/ml:10⁶ CFU/ml) | | | | | | | | | | |
|---|---|---|---|---|---|---|---|---|---|---|---|
| | Example 11 | Example 12 | Example 13 | Example 14 | Example 15 | Example 16 | Example 17 | Example 18 | Example 19 | Example 20 | Ceftazidime | Cefotaxime |
| 1. S. aureus 209P NIHJ-JC1 | 12.5 | 3.12 | 3.12 | 6.25 | 25 | 12.5 | 12.5 | 3.12 | 6.25 | 25 | 6.25 | 1.56 |
| 2. E. coli NIHJ JC2 | 0.05 | 0.39 | 0.2 | 0.78 | 0.39 | 0.78 | 0.1 | 0.2 | 0.05 | 0.39 | 0.1 | 0.05 |
| 3. E. coli CSH2(RK1)* | <0.006 | 0.025 | 0.006 | 0.0125 | 0.0125 | 0.05 | 0.025 | 0.025 | 0.025 | 0.2 | 0.1 | 0.0125 |
| 4. K. pneumoniae PCI-602 | <0.006 | <0.006 | <0.006 | <0.006 | <0.006 | <0.006 | 0.0125 | 0.025 | 0.0125 | 0.1 | 0.025 | <0.006 |
| 5. E. coli CSH(RE45)* | 0.05 | 0.025 | <0.006 | 0.025 | 0.05 | 1.56 | 0.1 | 0.1 | 0.1 | 0.78 | 0.2 | 0.1 |
| 6. K. oxytoca GN10650* | 0.025 | 0.1 | 0.025 | 0.1 | 0.1 | 0.1 | 0.1 | 0.2 | 0.05 | 0.39 | 0.1 | 0.39 |
| 7. K. pneumoniae No. 42* | 0.025 | 0.05 | 0.0125 | 0.05 | 0.1 | 0.025 | 0.05 | 0.2 | 0.2 | 0.78 | 0.39 | 0.05 |
| 8. P. vulgaris HX-19 | <0.006 | <0.006 | <0.006 | <0.006 | 0.0125 | <0.006 | <0.006 | <0.006 | <0.006 | <0.006 | 0.025 | <0.006 |
| 9. P. vulgaris No. 33* | 0.0125 | 0.025 | 0.025 | 0.025 | 0.05 | 0.025 | 0.0125 | 0.025 | <0.006 | 0.05 | 0.05 | 0.0125 |
| 10. S. marcescens IAN 1184 | 0.025 | 0.05 | 0.025 | 0.025 | 0.05 | 0.05 | 0.1 | 0.025 | <0.006 | <0.006 | <0.006 | 0.0125 |
| 11. E. cloacae 963 | 0.025 | 0.2 | 0.05 | 0.39 | 0.05 | 0.39 | 0.0125 | 0.78 | 0.1 | 3.12 | 0.1 | 0.05 |
| 12. E. cloacae Nek 39* | 0.1 | 0.1 | 0.2 | 0.1 | 0.39 | 0.78 | 3.12 | 0.39 | 0.78 | 1.56 | 1.56 | 1.56 |
| 13. E. coli GN5482* | 0.0125 | 0.39 | 0.05 | 1.56 | 0.025 | 0.05 | 1.56 | 0.0125 | 0.39 | 0.05 | 0.1 | 0.39 |
| 14. M. morganii GN5407* | 0.0125 | 0.05 | 0.05 | 0.05 | 0.025 | 0.05 | 0.025 | 0.0125 | 0.025 | 3.12 | 1.56 | 0.05 |
| 15. S. marcescens No. 16-2* | 0.2 | 0.78 | 0.78 | 0.39 | 0.78 | 0.78 | 3.12 | 3.12 | 1.56 | 3.12 | 1.56 | 6.25 |
| 16. Ps. aeruginosa IF03445 | 0.39 | 1.56 | 0.1 | 0.78 | 1.56 | 0.78 | 6.25 | 12.5 | 6.25 | 6.25 | 1.56 | 6.25 |
| 17. Ps. aeruginosa AK 109 | 0.2 | 3.12 | 1.56 | 3.12 | 1.56 | 1.56 | 6.25 | 12.5 | 6.25 | 12.5 | 0.78 | 25 |
| 18. Ps. aeruginosa AKR17 | 3.12 | 3.12 | <0.006 | 0.0125 | <0.006 | <0.006 | >100 | >100 | >100 | >100 | >100 | 12.5 |
| 19. Ps. cepacia 23 | <0.006 | 0.025 | 0.1 | 0.2 | 0.39 | <0.006 | 1.56 | 3.12 | 3.12 | 3.12 | 0.78 | >100 |
| 20. A. calcoaceticus No. 4 | 0.1 | 0.2 | 0.1 | 0.2 | 0.39 | 0.2 | 25 | 100 | 100 | 100 | 6.25 | 25 |

Further, the compounds of the present invention exhibit excellent pharmacokinetics. As a representative example, the compound of Example 15 was administered to mice by means of subcutaneous administration, and the concentration in the blood was measured.

Four week old ddY type male mice (weight: 19–22 g) were used in a group of 5 animals. The test compound was dissolved in a physiological sodium chloride solution to obtain a formulation having a concentration of 2 mg/ml. The formulation was subcutaneously administered to the mice in an amount of 0.1 ml per 10 g of the weight of the mice. 7.5, 15, 30, 60, 120 and 240 minutes after the administration, the blood was sampled from the heart of mice by means of a syringe treated with heparin. The concentration in the blood at each measurement is shown in the following Table.

Now, Ceftazidime was used as a comparative compound. Further, the antibacterial activities of the sample diluted by plasma to have an appropriate concentration were measured by the paper disk method using Morganella morganii IFO 3843 as the test bacterium.

As is evident from the results in the following Table, the compound of the present invention can promptly reach a high concentration in the blood and excellent as compared with that of Ceftazidime.

| Test compound | Dose (mg/kg) | Concentration in blood — Period after administration (min.) | | | | | |
| --- | --- | --- | --- | --- | --- | --- | --- |
| | | 7.5 | 15 | 30 | 60 | 120 | 240 |
| Example 15 | 20 | 33.8 | 45 | 44.3 | 21.9 | 7.1 | 7.2 |
| Ceftazidime | 20 | 25.4 | 24.1 | 17.3 | 3.3 | 0.2 | — |

(Unit: μg/ml)

The compounds of the present invention exhibit strong antibacterial activities against Gram-positive and Gram-negative bacteria and particularly excellent activities against resistant Gram-negative bacteria including Pseudmonas aeruginosa. Thus, the compounds of the formula I and non-toxic salts and their physiologically hydrolyzable non-toxic esters thereof are useful as antibacterial agents.

The compounds of the present invention may be mixed with a carrier of solid or liquid excipient which is known in this field, and may be used in the form of a pharmaceutical formulation suitable for parenteral administration, oral administration or external administration.

As the pharmacetical formulations, there may be mentioned liquid formulations such as injection solutions, syrups and emulsions, solid formulations such as tablets, capsules and granules and formulations for external application such as ointments and suppositories. Further, these formulations may optionally contain commonly employed additives such as assisting agents, stabilizers, wetting agents, emulsifying agents, absorption-promoting agents or surfactants. As such additives, distilled water for injection, a Ringer solution, glucose, sucrose syrup, gelatin, edible oil, coconut oil, ethylene glycol, sucrose, corn starch, magnesium stearate and talc, may be mentioned.

Further, the compounds of the present invention can be used as antibacterial agents for the treatment of human infectious diseases.

The dose may vary depending upon the condition such as the age or sex of the patient, and is usually within a range of from 1 to 100 mg/kg per day. It is preferred to administer a daily dose of from 5 to 30 mg/kg in 2 to 4 times.

Now, the present invention will be described in further detail with reference to Examples and Reference Examples. However, the present invention is by no means restricted thereto.

EXAMPLES

Example 1

Preparation of
7β-[2-(2-aminothiazol-4-yl)-2-(1-carboxy-1-vinyloxyimino)acetamido]-3-(1-pyridinio)methyl-3-cephem-4-carboxylate (syn-isomer)

(A) 5.06 g (9.76 mmol) of 2-(1-tert-butoxycarbonyl-1-vinyloxyimino)-2-(2-tritylaminothiazol-4-yl)acetic acid (syn-isomer) and 4.05 g (9.76 mmol) of benzhydryl 7β-amino-3-chloromethyl-3-cephem-4-carboxylate were dissolved in 100 ml of methylene chloride, and 5.56 ml (43.9 mmol) of N,N-dimethylaniline and 1.07 ml (11.5 mmol) of phosphorus oxychloride were dropwise added thereto at 0° C. The mixture was stirred for one hour. The reaction solution was washed sequentially with 0.5N hydrochloric acid and with a saturated sodium chloride aqueous solution. The extracted solution was dried over anhydrous sodium sulfate, and then the solvent was distilled off under reduced pressure to obtain 8.7 g (yield: 96.7%) of benzhydryl 7β-[2-(1-tert-butoxycarbonyl-1-vinyloxyimino)-2-(2-tritylaminothiazol-4-yl)acetamido]-3-chloromethyl-3-cephem-4-carboxylate (syn-isomer).

IR(KBr)cm$^{-1}$: 3400, 2960, 1790, 1720, 1520, 1150, 700

NMR(DMSO-d$_6$)δ: 1.48(9H, s), 3.47 and 3.75(2H, ABq, J=18 Hz), 4.45(2H, br s), 5.19(1H, br s), 5.27(1H, d, J=4.5 Hz), 5.35(1H, br s), 5.77(1H, dd, J=4.5 and 7.5 Hz), 6.92(1H, s), 6.95(1H, s), 7.30(25H, m), 8.86(1H, br s), 9.79(1H, d, J=7.5 Hz)

(B) 4 g (4.34 mmol) of the compound obtained in the above reaction (A) was dissolved in 80 ml of acetone, and 3.25 g (21.7 mmol) of sodium iodide was added thereto. The mixture was stirred at room temperature for one hour. The solvent was distilled off under reduced pressure. To the residue, 80 ml of ethyl acetate was added, and the mixture was washed sequentially with water, with a 10% sodium thiosulfate aqueous solution and with a saturated sodium chloride aqueous solution. The extracted solution was dried over anhydrous sodium sulfate. Then, the solvent was distilled off under reduced pressure, and the residue was washed with diisopropyl ether to obtain 3.98 g (yield: 90.5%) of benzhydryl 7β-[2-(tert-butoxycarbonyl-1-vinyloxyimino)-2-(2-tritylaminothiazol-4-yl)acetamido]-3-iodomethyl-3-cephem-4-carboxylate (syn-isomer).

(C) 304 mg (0.3 mmol) of the compound obtained in the above reaction (B) was dissolved in 6 ml of N,N-dimethylformamide, and 0.03 ml (0.36 mmol) of pyridine was added thereto. The mixture was stirred at room temperature for one hour. The solvent was distilled off under reduced pressure, and the residue was subjected to silica gel column chromatography (Wakogel C-300). The eluted fraction (8% methanol/chlorform) was concentrated to obtain 230 mg (yield: 85.4%) of benzhydryl 7β-[2-(1-tert-butoxycarbonyl-1-vinyloxyimino)-2-(2-tritylaminothiazol-4-yl)acetamido]-3-(1-pyridinio)methyl-3-cephem-4-carboxylate iodide (syn-isomer) as foamy substance.

(D) 280 mg (0.26 mmol) of the compound obtained in the above reaction (C) was dissolved in 4 ml of methylene chloride and 0.8 ml of anisole, and 8 ml of trifluoroacetic acid was added thereto under cooling with ice. The mixture was stirred for one hour. The solvent was distilled off, and to the residue, diethyl ether was added. The precipitates were collected by filtration. The precipitates were dissolved in 50 ml of a 10% methanol aqueous solution. Then, the solution was subjected to ODS column chromatography (LC-Sorb RP-18, Kemco Co.), and eluted with a 20% methanol aqueous solution. The eluted fraction containing the desired compound was concentrated and freeze-dried to obtain 70 mg (yield: 50%) of the above identified compound.

mp: 150° C. (decomposed)

IR(KBr)cm$^{-1}$: 3420, 1780, 1630, 1540, 1395, 1200

NMR(DMSO-d$_6$/D$_2$O)δ: 2.90–3.60(2H, ABq), 5.06(1H, d, J=4,5 Hz), 5.20–5.50(4H, m), 5.70(2H, d, J=4.5 Hz), 6.95(1H, s), 7.95(2H, m), 8.40(1H, m), 8.90(1H, m)

Example 2

Preparation of
7β-[2-(2-aminothiazol-4-yl)-2-(1-carboxy-1-vinyloxyimino)acetamido]-3-(2,3-cychlopenteno-1-pyridinio)-methyl-3-cephem-4-carboxylate (syn-isomer)

The same operations as in the steps (C) and (D) of Example 1 were conducted by using 234 mg (0.28 mmol) of benzhydryl 7β-[2-(1-tert-butoxycarbonyl-1-vinyloxyimino)-2-(2-tritylaminothiazol-4-yl)acetamido]-3-iodomethyl-3-cephem-4-carboxylate (syn-isomer) and 0.033 ml (0.28 mmol) of 2,3-cyclopentenopyridine. The product was subjected to ODS column chromatography and eluted with a 20% methanol aqueous solution to obtain 45 mg (yield: 28.1%) of the above-identified compound.

mp: 150° C. (decomposed)

IR(KBr)cm$^{-1}$: 3420 1770, 1620, 1540, 1400, 1200

NMR(DMSO-d$_6$/D$_2$O)δ: 2.15(2H, m , 2.80–3.30(6H, m), 5.05(2H, d, J=4.5 Hz), 5.10–5.30(4H, m), 5.66(1H, d, J=4.5 Hz), 6.93(1H, s), 7.60(1H, m), 8.15(1H, d, J=8 Hz), 8.45(1H, d, J=8 Hz)

Example 3

Preparation of
7β-[2-(2-aminothiazol-4-yl)-2-(1-carboxy-1-vinyloxyimino)acetamido]-3-(3-carboxy-1-pyridinio)methyl-3-cephem-4-carboxylate (syn-isomer)

The same operations as in steps of (C) and (D) of Example 1 were conducted by using 305 mg (0.3 mmol) of benzhydryl 7β-[2-(1-tert-butoxycarbonyl-1-vinyloxyimino)-2-(2-tritylaminothiazol-4-yl)acetamido]-3-iodomethyl-3-cephem-4-carboxylate (syn-isomer) and 95.6 mg (0.31 mmol) of benzhydryl nicotinate. The product was subjected to ODS column chromatography and eluted with a 20% methanol aqueous solution to obtain 31 mg (yield: 18.0%) of the above-identified compound.

mp: 130° C. (decomposed)

IR(KBr)cm$^{-1}$: 3400, 1770, 1640, 1620, 1390, 1200

NMR(DMSO-d$_6$/D$_2$O)δ: 3.10–3.80(2H, ABq), 5.10(1H, d, J=4.5 Hz), 5.25–5.50(4H, m), 5.70(1H, d, J=4.5 Hz), 6.93(1H, s), 8.00(1H, m), 8.70(1H, br s), 8.95(1H, br s), 9.25(1H, s)

Example 4

Preparation of
7β-[2-(2-aminothiazol-4-yl)-2-(1-carboxy-1-vinyloxyimino)acetamido]-3-(3-carbamoyl-1-pyridinio)methyl-3-cephem-4-carboxylate (syn-isomer)

The same operations as in steps of (C) and (D) of Example 1 were conducted by using 305 mg (0.3 mmol) of benzhydryl 7β-[2-(1-tert-butoxycarbonyl-1-vinyloxyimino)-2-(2-tritylaminothiazol-4-yl)acetamido]-3-iodomethyl-3-cephem-4-carboxylate (syn-isomer) and 38.4 mg (0.31 mmol) of nicotinamide. The product was subjected to ODS column chromatography and eluted with a 20% methanol aqueous solution to obtain 55.8 mg (yield: 32.4%) of the above-identified compound.

mp: 150° C. (decomposed)

IR(KBr)cm$^{-1}$: 3400, 1780, 1680, 1620, 1400, 1200

NMR(DMSO-d$_6$/D$_2$O)δ: 3.10–3.80(2H, ABq), 5.20(1H, d, J=4.5 Hz), 5.40–5.60(4H, m), 5.83(1H, d, J=4.5 Hz), 7.06(1H, s), 8.21(1H, m), 8.90(1H, br s), 9.20(1H, br s), 9.45(1H, s)

Example 5

Preparation of
7β-[2-(2-aminothiazol-4-yl)-2-(1-carboxy-1-vinyloxyimino)acetamido]-3-(4-carboxy-1-pyridinio)methyl-3-cephem-4-carboxylate (syn-isomer)

The same operations as in steps of (C) and (D) of Example 1 were conducted by using 203 mg (0.2 mmol) of benzhydryl 7β-[2-(1-tert-butoxycarbonyl-1-vinyloxyimino)-2-(2-tritylaminothiazol-4-yl)acetamido]-3-iodomethyl-3-cephem-4-carboxylate (syn-isomer) and 203 mg (0.2 mmol) of benzhydryl isonicotinate. The product was subjected to ODS column chromatography and eluted with a 20% methanol aqueous solution to obtain 36 mg (yield: 31.3%) of the above-identified compound.

mp: 150° C. (decomposed)

IR(KBr)cm$^{-1}$: 3420, 1780, 1630, 1380, 1200

NMR(DMSO-d$_6$/D$_2$O)δ: 3.10–3.75(2H, ABq), 5.22(1H, d, J=4.5 Hz), 5.40–5.70(4H, m), 5.85(1H, d, J=4.5 Hz), 7.10(1H, s), 8.30(2H, d, J=6 Hz), 9.05(2H, d, J=6 Hz)

Example 6

Preparation of
7β-[2-(2-aminothiazol-4-yl)-2-(1-carboxy-1-vinyloxyimino)acetamido]-3-(4-carbamoyl-1-pyridinio)methyl-3-cephem-4-carboxylate (syn-isomer)

The same operations as in the steps of (C) and (D) of Example 1 were conducted by using 203 mg (0.2 mmol) of benzhydryl 7β-[2-(1-tert-butoxycarbonyl-1-vinyloxyimino)-2-(2-tritylaminothiazol-4-yl)acetamido]-3-iodomethyl-3-cephem-4-carboxylate (syn-isomer) and 25.6 mg (0.21 mmol) of isonicotinamide. The product was subjected to ODS column chromatography and eluted with a 20% methanol aqueous solution to obtain 31 mg (yield: 27.0%) of the above-identified compound.

mp: 160° C. (decomposed)

IR(KBr)cm$^{-1}$: 3420, 1780, 1670, 1630, 1540, 1400, 1350, 1200

NMR(DMSO-d$_6$/D$_2$O)δ: 3.10–3.70(2H, ABq), 5.10(1H, d, J=4.5 Hz), 5.30–5.55(4H, m), 5.75(1H, d, J=4.5 Hz), 7.00 (1H, s), 8.30(2H, d, J=6 Hz), 9.10(2H, d, J=6 Hz)

Example 7

Preparation of
7β-[2-(2-aminothiazol-4-yl)-2-(1-carboxy-1-vinyloxyimino)acetamido]-3-(4-sulfonatomethyl-1-pyridinio)-methyl-3-cephem-4-carboxylic acid (syn-isomer)

(A) 773 mg (0.75 mmol) of benzhydryl 7β-[2-(1-tert-butoxycarbonyl-1-vinyloxyimino)-2-(2-tritylaminothiazol-4-yl)acetamido]-3-iodomethyl-3-cephem-4-carboxylate 1-oxide (syn-isomer) was dissolved in 5 ml of N,N-dimethylformamide, and 293 mg (1.5 mmol) of potassium 4-pyridylmethanesulfonate was added thereto. The mixture was left to stand at room temperature for 2 hours. The solvent was distilled off under reduced pressure, and the residue was subjected to silica gel column chromatography (Wakogel C-300) to obtain 650 mg (yield: 70.7%) of benzhydryl 7β-[2-(1-tert-butoxycarbonyl-1-vinyloxyimino)-2-(2-tritylaminothiazol-4-yl)acetamido]-3-(4-sulfonatomethyl-1-pyridinio)methyl-3-cephem-4-carboxylate 1-oxide (syn-isomer) as foamy substance.

(B) 650 mg (0.53 mmol) of the compound obtained in the above reaction (A) was dissolved in 4 ml of N,N-dimethylformamide, and 0.13 ml (1.5 mmol) of phosphorus trichloride was added thereto at −40° C. The reaction solution was stirred at a temperature of from −20° to −40° C. for 2 hours. Then, the reaction solution was poured into ice water, and the precipitates were collected by filtration. This precipitates were dissolved in methylene chloride, and the solution was dried over anhydrous sodium sulfate. Then, the solvent was distilled off under reduced pressure to obtain 510 mg (yield: 79.5%) of benzhydryl.7β-[2-(1-tert-butoxycarbonyl-1-vinyloxyimino)-2-(2-tritylaminothiazol-4-yl)acetamido]-3-(4-sulfonatomethyl-1-pyridinio)methyl-3-cephem-4-carboxylate (syn-isomer). The product was used for the subsequent reaction without purification.

(C) 500 mg (0.41 mmol) of the compound obtained in the above reaction (B) was subjected to the same operation as in step of (D) of Example 1. The product was subjected to ODS column chromatography and eluted with a 20% methanol aqueous solution to obtain 94.2 mg (yield: 35.7%) of the above-identified compound.

mp: 130° C. (decomposed)
IR(KBr)cm$^{-1}$: 3450, 1780, 1640, 1400, 1200, 1040
NMR(DMSO-d$_6$/D$_2$O) δ: 3.20–3.60(2H, ABq), 4.20(2H, s), 5.20(1H, d, J=4.5 Hz), 5.30–5.60(4H, m), 5.86(1H, d, J=4.5 Hz), 7.00(1H, s), 8.05(2H, d, J=6 Hz), 8.90(2H, d, J=6 Hz)

Example 8

Preparation of
7β-[2-(2-aminothiazol-4-yl)-2-(1-carboxy-1-vinyloxyimino)acetamido]-3-[4-(2-sulfonatoethyl)-1-pyridinio]-methyl-3-cephem-4-carboxylic acid (syn-isomer)

The same operation as in Example 7 was conducted by using 773 mg (0.75 mmol) of benzhydryl 7β-[2-(1-tert-butoxycarbonyl-1-vinyloxyimino)-2-(2-tritylaminothiazol-4-yl)acetamido]-3-iodomethyl-3-cephem-4-carboxylate 1-oxide (syn-isomer) and 328 mg 1.5 mmol) of potassium 2-(4-pyridyl)ethanesulfonate. The product was subjected to ODS column chromatography and eluted with a 20% methanol aqueous solution to obtain 76 mg of the above-identified compound.

mp: 130° C. (decomposed)
IR(KBr)cm$^{-1}$: 3450, 1780, 1630, 1520, 1400, 1200
NMR(DMSO-d$_6$/D$_2$O)δ: 3.20–3.16(2H, ABq), 3.30–3.70(4H, m), 5.20(1H, d, J=4.5 Hz), 5.30–5.60(4H, m), 5.75(1H, d, J=4.5 Hz), 6.96(1H, s), 8.15(2H, d, J=6 Hz), 9.10(2H, d, J=6 Hz)

Example 9

Preparation of sodium
7β-[2-(2-aminothiazol-4-yl)-2-(1-carboxylato-1-vinyloxyimino)acetamido]-3-(3-amino-1-pyridinio)methyl 3-cephem-4-carboxylate (syn-isomer)

The same operations as in steps of (A), (B) and (C) of Example 7 were conducted by using 773 mg (0.75 mmol) of benzhydryl 7β-[2-(1-tert-butoxycarbonyl-1-vinyloxyimino)-2-(2-tritylaminothiazol-4-yl)acetamido]-3-iodomethyl-3-cephem-4-carboxylate 1-oxide (syn-isomer) and 276.5 mg (0.83 mmol) of 3-tritylaminopyridine. The trifluoroacetate obtained in step of (C) was adjusted to pH 6.5 with a sodium bicarbonate aqueous solution, then subjected to ODS column chromatography and eluted with a 5% methanol aqueous solution to obtain 23 mg (yield: 5.4%) of the above-identified compound.

mp: 125° C. (decomposed)
IR(KBr)cm$^{-1}$: 3400, 1770, 1620, 1540, 1400, 1200
NMR(DMSO-d$_6$/D$_2$O)δ: 3.20–3.60(2H, ABq), 5.00–5.25(5H, m), 5.65(1H, d, J=4.5 Hz), 6.90(1H, s), 7.60–8.40 (4H, m)

Example 10

Preparation of sodium
7β-[2-(2-aminothiazol-4-yl)-2-(1-carboxylato-1-vinyloxyimino)acetamido]-3-(3-formylamino-1-pyridinio)methyl-3-cephem-4-carboxylate (syn-isomer)

The same operation as in Example 9 was conducted by using 773 mg (0.75 mmol) of benzhydryl 7β-[2-(1-tert-butoxycarbonyl-1-vinyloxyimino)-2-(2-tritylaminothiazol-4-yl)acetamido]-3-iodomethyl-3-cephem-4-carboxylate 1-oxide (syn-isomer) and 101 mg (0.83 mmol) of 3-formylaminopyridine. The product was subjected to ODS column chromatography and eluted with a 5% methanol aqueous solution to obtain 125 mg (yield: 27.9%) of the above-identified compound.

mp: 120° C. (decomposed)
IR(KBr)cm$^{-1}$: 3400, 1770, 1660, 1600, 1540, 1500, 1400
NMR(DMSO-d$_6$/D$_2$O)δ: 3.20–3.60(2H, ABq), 4.95–5.20(4H, m), 5.05(1H, d, J=4.5 Hz), 5.70(1H, d, J=4.5 Hz), 6.85 (1H, s), 7.60–8.40(4H, m), 9.45(1H, s)

Example 11

Preparation of disodium
7β-[2-(2-aminothiazol-4-yl)-2-(1-carboxy-1-vinyloxyimino)acetamido]-3-[5-(3,4-dihydroxyphenyl)-1,3,4-oxadiazol-2-yl]thiomethyl-3-cephem-4-carboxylate (syn-isomer)

(A) 461 mg (0.5 mmol) of benzhydryl 3-chloromethyl-7β-[2-(1-tert-butoxycarbonyl-1-vinyloxyimino)-2-(2-tritylaminothiazol-4-yl acetamido]-3-cephem-4-carboxylate (syn-isomer) was dissolved in 8 ml of N,N-dimethylforamide, and 375 mg (2.35 mmol) of sodium iodide was added thereto. The mixture was stirred at room temperature for 50 minutes. To the reaction solution, 105 mg (0.5 mmol) of 5-(3,4-dihydroxyphenyl)-2-mercapto-1,3,4-oxadiazole was added, and the mixture was stirred for 1 hour. To the reaction solution, 50 ml of ethyl acetate was added, and the mixture was washed with water and then dried over anhydrous sodium sulfate. The solvent was distilled off under reduced pressure. To the residue, diethyl ether was added to obtain 420 mg of crude benzhydryl 7β-[2-(1-tert-butoxycarbonyl-1-vinyloxyimino)-2-(2-tritylaminothiazol-4-yl)acetamido]-3-[5-(3,4-dihydroxyphenyl)-1,3,4-oxadiazol-2-yl]thiomethyl-3-cephem-4-carboxylate. The crude product was used for the subsequent reaction without purification.

(B) 440 mg (0.36 mmol) of the compound obtained in the above reaction (A) was dissolved in 5 ml of methylene chloride and 1 ml of anisole, and the solution was cooled to 0° C. A solution of 5 ml of methylene chloride and 10 ml of trifluoroacetic acid which was previously cooled to 0° C., was added thereto all at once. The mixture was stirred for 1 hour. The solvent was distilled off under reduced pressure. To the residue, diethyl ether was added, and the precipitates were collected by filtration. The precipitates were suspended in water. The suspension was adjusted to pH 7.1 with a saturated sodium bicarbonate aqueous solution and then subjected to reversed phase column chromatography (LC-Sorb RP-18, manufactured by Kemco Co.) and eluted with a 8% methanol aqueous solution. The eluted fraction containing the desired compound was concentrated and freeze-dried to obtain 114 mg (yield: 44%) of the above-identified compound.

mp: 190° C. (decomposed)
IR(KBr)cm$^{-1}$: 3400, 1760, 1600, 1400
NMR(D$_2$O)δ: 3.45 and 3.78(2H, ABq, J=17.5 Hz), 4.17(2H, br s), 5.17(1H, d, J=4.5 Hz), 5.22(1Hd, J=2 Hz), 5.36(1H, d, J=2 Hz), 5.82(1H, d, J=4.5 Hz), 6.84(1H, br s), 7.10-7.20(3H, m)

Example 12

Preparation of disodium 7β-2-(2-aminothiazol-4-yl)-2-(1-carboxylato-1-vinyloxyimino)acetamido]-3-[4-(3,4-dihydroxyphenyl)thiazol-2-yl]thiomethyl-3-cephem-4-carboxylate (syn-isomer)

(A) The same operation as in step (A) of Example 11 was conducted by using 1.17 g (1.12 mmol) of benzhydryl 7β-[2-(1-tert-butoxycarbonyl-1-vinyloxyimino)-2-(2-tritylaminothiazol-4-yl)acetamido]-3-iodomethyl-4-carboxylate (syn-isomer) and 0.3 g (1.33 mmol) of 4-(3,4-dihydroxyphenyl)-2-mercaptothiazole to obtain 0.96 g (yield: 74.9%) of benzhydryl7β-[2-(1-tert-butoxycarbonyl-1-vinyloxyimino)-2-(2-tritylaminothiazol-4-yl)acetamido]-3-[4-(3,4-dihydroxyphenyl]thiazol-2-yl]thiomethyl-3-cephem-4-carboxylate (syn-isomer).

NMR(DMSO-d$_6$)δ: 1.42(9H, s), 37.0(2H, m), 4.20(1H, d, J=14 Hz), 4.46(1H, d, J=14 Hz), 5.15(1H, br s), 5.18 (1H, d, J=5 Hz), 5.32(1H, br s), 5.72(1H, m), 6.73 (1H, s), 6.85(1H, s), 6.94(1H, s), 7.00-7.70(27H, m)

(B) 0.96 g (0.84 mmol) of the compound obtained in the above reaction (A) was subjected to the same operation as in step (B) of Example 11 to obtain 225 mg (yield: 41.4%) of the above-identified compound.

mp: 110° C. (decomposed)
IR(KBr)cm$^{-1}$: 3400, 1742, 1517
NMR(DMSO-d$_6$)δ: 3.53(2H, m), 4.48(2H, m), 4.88(1H, br s), 5.01(1H, d, J=4 Hz), 5.18(1H, br s), 5.65(1H, m), 6.78(1H, d, J=9 Hz), 6.90(1H, s), 7.18(1H, dd, J=2 and 9 Hz), 7.76(1H, d, J=2 Hz), 7.56(1H, s)

EXAMPLE 13

Preparation of disodium 7β-[2-(2-aminothiazol-4-yl)-2-(1-carboxylato-1-vinyloxyimino)acetamido]-3-[5-(3,4-dihydroxyphenyl)-1,3,4-thiadiazol-2-yl]thiomethyl-3-cephem-4-carboxylate (syn-isomer)

(A) The same operation as in step (A) of Example 11 was conducted by using 1.0 g (0.96 mmol) of benzhydryl 7β-[2-(1-benzhydryloxycarbonyl-1-vinyloxyimino)-2-(2-tritylaminothiazol-4-yl)acetamido]-3-iodomethyl-3-cephem-4-carboxylate (syn-isomer) and 0.24 g (1.06 mol) of 5-(3,4-dihydroxyphenyl)-2-mercapto-1,3,4-thiadiazole to obtain 425 mg (yield: 41%) of benzhydryl 7β- 2-(1-tert-butoxycarbonyl-1-vinyloxyimino)-2-(2-tritylaminothiazol-4-yl)acetamido]-3-[5-(3,4-dihydroxyphenyl)-1,3,4-thiadiazol-2-yl]thiomethyl-3-cephem-4-carboxylate (syn-isomer) as foamy substance.

NMR(DMSO-d$_6$)δ: 1.47(9H, s, 3.70(2H, m), 4.20(1H, br d, J-12 Hz), 4.52(1H, br d, J=12 Hz), 5.20(1H, br s), 5.22 (1H, d, J=5 Hz), 5.35(1H, br s), 5.75(1H, m), 6.88 (1H, m), 6.90(1H, s), 7.00-7.70(27H, m), 8.88(1H, m), 9.78(1H, m)

(B) 451 mg (0.39 mmol) of the compound obtained in the above reaction (A) was subjected to the same operation as in step (B) of Example 11 to obtain 68 mg (yield: 24%) of the above-identified compound.

mp: 160° C. (decomposed)
IR(KBr)cm$^{-1}$: 3430, 1765, 1600, 1540
NMR(DMSO-d$_6$)δ: 3.53(2H, m), 4.50(2H, m), 4.92(1H, br s), 5.05(1H, d, J=4 Hz), 5.22(1H, br s), 5.66(1H, m), 6.90 (1H, m), 6.92(1H, s), 7.15(1H, m), 7.30(1H, br s)

Example 14

Preparation of disodium 7β-[2-(2-aminothiazol-4-yl)-2-(1-carboxylato-1-vinyloxyimino)acetamido]-3-[5-(3,4-dihydroxyphenyl)oxazol-2-yl]thiomethyl-3-cephem-4-carboxylate (syn-isomer)

(A) The same operation as in step (A) of Example 11 was conducted by using 1.0 g (1.06 mmol) of benzhydryl 7β-[2-(1-tert-butoxycarbonyl-1-vinyloxyimino)-2-(2-tritylaminothiazol-4-yl)acetamido]-3-chloromethyl-3-cephem-4-carboxylate (syn-isomer), 175 mg (1.17 mmol) of sodium iodide and 0.260 g (1.21 mmol) of 5-(3,4-dihydroxyphenyl)-2-mercaptooxazole to obtain 0.75 g (yield: 63.2%) of benzhydryl 7β-[2-(1-tert-butoxycarbonyl-1-vinyloxyimino)-2-(2-tritylaminothiazol-4-yl)acetamido]-3-[5-(3,4-dihydroxyphenyl)oxazol-2-yl]thiomethyl-3-cephem-4-carboxylate (syn-isomer).

IR(KBr)cm$^{-1}$: 1790, 1720, 1660, 1530, 1370, 1150, 700

NMR(DMSO-d$_6$)δ: 1.40(9H, s), 3.55-3.80(2H, m), 3.90-4.35 (2H, m), 5.10-5.35(3H, m), 5.70(1H, m), 6.70-7.70 (31H, m), 9.25(1H, m)

(B) 0.72 g (0.64 mmol) of the compound obtained in the above reaction (A) was subjected to the same operation as in step (B) of Example 11. The trifluoroacetate thereby obtained was suspended in water. The suspension was adjusted to pH 6.5 with a saturated sodium bicarbonate aqueous solution, and then the insolubles were removed by filtration. The filtrate was subjected to reversed phase column chromatography (LC-Sorb RP-18, manufactured by Kemco Co.). The eluted fractions containing the desired compound (eluted with a 3% methanol aqueous solution), were gathered, concentrated and freeze-dried to obtain 110 mg (yield: 27.2%) of the above-identified compound.

mp: 190° C. (decomposed)

IR(KBr)cm$^{-1}$: 1760, 1600, 1530, 1400, 1280, 1200, 1010

NMR(DMSO-d$_6$/D$_2$O)δ: 3.30–3.70(2H, m), 4.30(2H, br s), 4.80–5.25((3H, m), 5.63(1H, m), 6.75–7.15(4H, m), 7.33(1H, s)

Example 15

Preparation of trisodium 7β-[2-(2-aminothiazol-4-yl)-2-(1-carboxylato-1-vinyloxyimino)acetamido]-3-[4-carboxylato-5-(3,4-dihydroxyphenyl)thiazol-2-yl]thiomethyl-3-cephem-4-carboxylate (syn-isomer)

(A) 11.43 g (12 mmol) of benzhydryl 7β-[2-(1-tert-butoxycarbonyl-1-vinyloxyimino)-2-(2-tritylaminothiazol-4-yl)acetamido]-3-chloromethyl-3-cephem-4-carboxylate (syn-isomer) was dissolved in 90 ml of N,N-dimethylformamide, and 8.3 g (55 mmol) of sodium iodide was added thereto. The mixture was stirred at room temperature for 1 hour. To the reaction solution, 3.23 g (12 mmol) of 4-carboxy-5-(3,4-dihydroxyphenyl)-2-mercaptothiazole and 1.67 ml (12 mmol) of triethylamine were added, and the mixture was stirred at the same temperature for 45 minutes. The solvent was distilled off under reduced pressure. To the residue, 500 ml of ethyl acetate and 150 ml of water were added, and the mixture was adjusted to pH 1.5 with 2N hydrochloric acid. The organic layer was washed with 150 ml of a 5% sodium thiosulfate aqueous solution and with 150 ml of a saturated sodium chloride aqueous solution, then dried over anhydrous magnesium sulfate and concentrated under reduced pressure. The residue was subjected to silica gel column chromatrography (Wakogel C-300, eluted with 2% methanol/chloroform) to obtain 8.33 g (yield: 59%) of benzhydryl 7β-[2-(1-benzhydryloxycarbonyl-1-vinyloxyimino)-2-(2-tritylaminothiazol-4-yl)acetamido]-3-[4-carboxy-5-(3,4-dihydroxyphenyl)thiazol-2-yl]thiomethyl-3-cephem-4-carboxylate (syn-isomer).

IR(KBr)cm$^{-1}$: 1790, 1720, 1680, 1640, 1530, 1500, 1370, 1280, 1200, 1150

NMR(DMSO-d$_6$)δ: 1.46(9H, s , 3.75(2H, ABq), 4.27 (2H, ABq), 5.19((1H, s), 5.22(1H, d, J=4.5 Hz), 5.35 (1H, s), 5.75(1H, dd, J=4.5 and 9 Hz), 6.77(2H, s), 6.93(2H, s), 6.96(1H, s), 7.35(25H, s), 8.86 (1H, br s), 9.16(1H, br s), 9.33(1H, br s), 9.77(1H, d, J=9 Hz)

(B) 8.30 g of the compound obtained by the above reaction (A) was dissolved in 38 ml of methylene chloride and 7.6 ml of anisole, and 38 ml of trifluoroacetic acid was dropwise added thereto over a period of 20 minutes at −10° C. The mixture was stirred at room temperature for 2 hours. The reaction solution was concentrated under reduced pressure, and 200 ml of diisopropyl ether was added to the oily residue. The precipitated insolubles were collected by filtration. The precipitated insolubles were washed with diisopropyl ether (50 ml×2 times) and dried under reduced pressure to obtain 5.53 g (yield: 85%) of the trifluoroacetate of the above-identified compound as powder.

NMR(DMSO-d$_6$)δ: 3.73(2H, ABq), 4.35(2H, ABq), 5.19(1H, d, J=4.5 Hz),5.41(1H, s), 5.48(1H, s), 5.83(1H, dd, J=4.5 and 9 Hz), 6.0–7.2(4H, m), 6.78(2H, s), 6.91(1H, s), 7.03(1H, s), 9.83(1H, d, J=9 Hz)

(C) 5.45 g (7.26 mmol) of the compound obtained in the above reaction (B) was suspended in 80 ml of water, and the suspension was adjusted to pH 7.3 with a saturated sodium bicarbonate aqueous solution under cooling with ice. The insolubles were removed by filtration. The filtrate was subjected to reversed phase column chromatography (LC-Sorb RP-18, manufactured by Kemco Co., eluted with water). The eluted fraction containing the desired compound was concentrated and freeze-dried to obtain 2.51 g (yield: 44%) of the above-identified compound.

mp: 270° C. (decomposed)

IR(KBr)cm$^{-1}$: 1760, 1670, 1595, 1540, 1405

NMR(D$_2$O)6 3.57(2H, ABq), 4.18 2H, ABq), 5.17(1H, d, J=4.5 Hz), 5.19(1H, s), 5.34(1H, s), 5.80(1H, d, J=4.5 Hz), 6.88(2H, s), 6.98(1H, s), 7.17(1H, s)

Example 16

Preparation of trisodium 3-[4-(3,4-diacetoxyphenyl)-5-carboxylatomethylthiazol-2-yl]thiomethyl-7β-[2-(2-aminothiazol-4-yl)-2-(1-carboxylato-1-vinyloxyimino)acetamido]-3-cephem-4-carboxylate (syn-isomer)

(A) 5.0 g (9.01 mmol) of 2-(1-tert-butoxycarbonyl-1-vinyloxyimino)-2-(2-tritylaminothiazol-4-yl)acetic acid (syn-isomer) and 3.73 g (9.0 mmol) of benzhydryl 7β-amino-3-chloromethyl-3-cephem-4-carboxylate were dissolved in 80 ml of methylene chloride, and 5.11 ml (40.5 mmol) of N,N-dimethylaniline and then 1.01 ml (10.8 mmol) of phosphorus oxychloride were dropwise added thereto under cooling with ice. The mixture was stirred at room temperature for 1 hour. Then, the reaction solution was washed sequentially with 0.5N hydrochloric acid and with a saturated sodium chloride aqueous solution and dried over anhydrous sodium sulfate. The solvent was distilled off under reduced pressure to obtain the foamy residue of benzhydryl 7β-[2-(1-tert-butoxycarbonyl-1-vinyloxyimino)-2-(2-tritylaminothiazol-4-yl)acetamido]-3-chloromethyl-3-cephem-4-carboxylate (syn-isomer). The product was used for the subsequent reaction without purification.

(B) The compound obtained in the above reaction (A) was dissolved of 200 ml of acetone, and 2.7 g (18 mmol) of sodium iodide was added thereto. The mixture was stirred at room temperature for 30 minutes. The solvent was distilled off under reduced pressure, and to the residue, ethyl acetate was added. The mixture was washed with water and with a saturated sodium chloride aqueous solution and dried over anhydrous sodium sulfate. The solvent was distilled off to obtain 10.2 g of benzhydryl 7β-[2-(1-tert-butoxycarbonyl-1-vinyloxyimino)-2-(2-tritylaminothiazol-4-yl)acetamido]-3-iodomethyl-3-cephem-4-carboxylate (syn-isomer).

NMR(DMSO-d$_6$)δ: 1.48(9H, s), 3.30–3.90(2H, m), 4.35 (2H, m), 5.18(1H, br s), 5.22(1H, d, J=5.0 Hz), 5.36(1H, br s), 5.75(1H, m), 6.90–7.80(27H, m), 8.88 (1H, br s), 9.80(1H, br d, J=8.0 Hz)

(C) 1.13 g (about 1.08 mmol) of the crude product obtained in the above reaction (B) was dissolved in 10 ml of N,N-dimethylformamide, and 0.58 g (1.09 mmol) of 4-(3,4-diacetoxyphenyl)-5-benzhydryloxycarbonylmethyl-2-mercaptothiazole was added thereto. The mixture was stirred at room temperature for 1 hour. The solvent was distilled off under reduced pressure to obtain benzhydryl 3-[4-(3,4-diacetoxyphenyl)-5-benzhydryloxycarbonylmethylthiazol-2-yl]thiomethyl-7β-[2-(1-tert-butoxycarbonyl-1-vinyloxyimino)-2-(2-tritylaminothiazol-4-yl)acetamido]-3-cephem-4-carboxylate (syn-isomer). The product was used for the subsequent reaction without purification.

(D) The crude product obtained in the above reaction (C) was dissolved in 5.0 ml of methylene chloride and 1.0 ml of anisole, and 5.0 ml of trifluoroacetic acid was added thereto under cooling with ice. The mixture was stirred for 1 hour. The solvent was distilled off under reduced pressure, and to the residue, diethyl ether was added. The precipitates were collected by filtration and suspended in water. The suspension was adjusted to pH 6.5 with a saturated sodium bicarbonate aqueous solution, then subjected to reversed phase column chromatography (LC-Sorb RP-18, manufactured by Kemco Co.) and eluted with a 5% methanol aqueous solution. The eluted fractions containing the desired compound were gathered, concentrated and freeze-dried to obtain 122 mg (yield based on step (B):.13%).

mp: 180°–185° C. (decomposed)

IR(KBr)cm$^{-1}$: 3400, 1760, 1590, 1535, 1370, 1210

NMR(DMSO-d$_6$)δ: 2.30(6H, s), 4.10–4.80(2H, m), 4.95(1H, br s), 5.03(1H, d, J=5.0 Hz), 5.22(1H, br s), 5.62(1H, m), 6.95(1H, s , 7.20–7.70(3H, m)

Example 17

Preparation of disodium 7β-[2-(2-aminothiazol-4-yl)-2-(1-carboxylato-1-vinyloxyimino)acetamido]cephalosporanate (syn-isomer)

(A) To a mixed solution of 0.18 ml (1.93 mmol) of phosphorus oxychloride and 0.544 ml of ethyl acetate, 0.15 ml (1.93 mmol) of N,N-dimethylformamide was added, and the mixture was stirred at room temperature for 30 minutes. Then, the reaction solution was cooled to 0° C., and 2 ml of ethyl acetate and 841 mg (1.51 mmol) of 2-(1-tert-butoxy-carbonyl-1-vinyloxyimino)-2-(2-tritylaminothiazol-4-yl)-acetic acid (syn-isomer) were added thereto. The mixture was stirred for 1 hour. A suspension of 546 mg (2 mmol) of 7β-aminocephalosporanic acid in 8 ml of acetone and 12 ml of water, was adjusted to pH 7.5 with a 2N sodium hydroxide aqueous solution and then dropwise added to the solution containing the reactive derivative of the carboxylic acid as previously prepared over a period of 20 minutes while keeping the solution at pH 7.5 to 8.5. Further, the mixture was stirred for 1 hour. To the reaction solution, 50 ml of ethyl acetate was added, and the mixture was adjusted to pH 2.0 with 4N hydrochloric acid. The insolubles were removed by filtration. The organic layer was washed with a saturated sodium chloride aqueous solution and then dried over anhydrous sodium sulfate. The solvent was distilled off under reduced pressure, and the residue was subjected to silica gel column chromatography (Wakogel C-300, eluted with 0 to 4% methanol/chloroform). The eluted fraction containing the desired compound was concentrated to obtain 600 mg (yield: 20 49.1%) of 7β-[2-(1-tert-butoxycarbonyl-1-vinyloxyimino)-2-(2-tritylaminothiazol-4-yl)acetamido]cephalosporanic acid (syn-isomer).

IR(KBr)cm$^{-1}$: 3400, 2960, 1790, 1720, 1530, 1220, 1150

NMR(DMSO-d$_6$)δ: 1.45(9H, s), 2.00(3H, s), 2.60–2.90 (2H, m), 4.63 and 4.96(2H, ABq, J=13 Hz), 5.06(1H, d, J=5 Hz), 5.13(1H, s), 5.30(1H, s), 5.65(1H, dd, J=5 and 7.5 Hz), 6.88(1H, s), 7.30(15H, s), 8.83(1H, br s), 9.70(1H, d, J=7.5 Hz)

(B) 560 mg (0.69 mmol) of the compound obtained in the above reaction (A) was dissolved in 3 ml of methylene chloride and 0.6 ml of anisole, and the solution was cooled with ice. Then, to the solution, a mixed solution of 6 ml of trifluoroacetic acid and 3 ml of methylene chloride which was previously cooled to 0° C. was added all at once, and the mixture was stirred at the same temperature for 30 minutes and at room temperature for 1 hour. The solvent was distilled off under reduced pressure, and to the residue, diisopropyl ether was added to obtain powder. The powder was suspended in 5 ml of water, and the suspension was adjusted to pH 6.5 with a 1N sodium hydrogencarbonate aqueous solution. The insolubles were removed by filtration. Then, the filtrate was subjected to reversed phase column chromatography (LC-Sorb RP-18, manufactured by Kemco Co., eluted with water). The eluted fraction containing the desired compound was concentrated and freeze-dried to obtain 228 mg (yield: 59.5%) of the above-identified compound.

mp: 150°–155° C. (decomposed)

IR(KBr)cm$^{-1}$: 3400, 1770, 1600, 1520, 1400

NMR(DMSO-d$_6$/TFA)δ: 2.05(3H, s), 3.36 and 3.65(2H, ABq, J=18 Hz), 4.67 and 5.00(2H, ABq, J=15 Hz), 5.15(1H, d, J=5 Hz), 5.33(1H, s), 5.43(1H, s), 5.80(1H, dd, J=5 and 8 Hz), 6.99(1H, s), 9.75(1H, d, J=8 Hz)

Example 18

Preparation of disodium 7β-[2-(2-aminothiazol-4-yl)-2-(1-carboxylato-1-vinyloxyimino)acetamido]-3-(5-methyl-1,3,4-thiadiazol-2-yl)thiomethyl-3-cephem-4-carboxylate (syn-isomer)

(A) The same operation as in step (A) of Example 17 was conducted by using 841 mg (1.51 mmol) of 2-(1-tert-butoxycarbonyl-1-vinyloxyimino)-2-(2-tritylaminothiazol-4-yl)acetic acid (syn-isomer) and 625 mg (2 mmol) of 7β-amino-3-(5-methyl-1,3,4-thiadiazol-2-yl)thiomethyl-3-cephem-4-carboxylic acid to obtain 480 mg (yield: 37.4%) of 7β-[2-(1-tert-butoxycarbonyl-1-vinyloxyimino)-2-(2-tritylaminothiazol-4-yl)acetamido]-3-(5-methyl-1,3,4-thiadiazol-2-yl)thiomethyl-3-cephem-4-carboxylic acid (syn-isomer).

IR(KBr)cm$^{-1}$: 3400, 2960, 1790, 1720, 1690, 1530, 1370, 1150

NMR(DMSO-d$_6$)δ: 1.45(9H, s), 2.66(3H, s), 3.75(2H, ABq, J=18 Hz), 4.19 and 4.51(2H, ABq, J=15 Hz), 5.10(1H, d, J=5 Hz), 5.13(1H, s), 5.31(1H, s), 5.63(1H, dd, J=5 and 8 Hz), 6.90(1H, s), 7.30(15H, br s), 8.80(1H, br s), 9.70(1H, d, J=8 Hz)

(B) 440 mg (0.52 mmol) of the compound obtained in the above reaction (A) was subjected to the same operation as in step (B) of Example 17 to obtain 185 mg (yield: 57.0%) of the above-identified compound.

mp: 157°–160° C. (decomposed)

IR(KBr)cm$^{-1}$: 3400, 1760, 1600, 1400, 1210

NMR(D$_2$O)δ: 2.72(3H, s), 3.38 and 3.80(2H, ABq, J=17 Hz), 3.96(2H, ABq), 5.18(2H, d, J=5 Hz), 5.20(1H, s), 5.35 (1H, s), 5.82(1H, d, J=5 Hz), 7.16(1H, s)

Example 19

Preparation of disodium 7β-[2-(2-aminothiazol-4-yl)-2-(1-carboxylato-1-vinyloxyimino)acetamido]-3-(1-methyl-1H-tetrazol-5-yl)thiomethyl-3-cephem-4-carboxylate (syn-isomer)

(A) The same operation as in step (A) of Example 17 was conducted by using 841 mg (1.51 mmol) of 2-(1-tert-butoxycarbonyl-1-vinyloxyimino)-2-(2-tritylaminothiazol-4-yl)acetic acid (syn-isomer) and 657 mg (2 mmol) of 7β-amino-3-(1-methyl-1H-tetrazol-5-yl)thiomethyl-3-cephem-4-carboxylic acid to obtain 670 mg (yield: 51.2%) of 7β-[2-(1-tert-butoxycarbonyl-1-vinyloxyimino)-2-(2-tritylaminothiazol-4-yl)acetamido]-3-(1-methyl-1H-tetrazol-5-yl)thiomethyl-3-cephem-4-carboxylic acid (syn-isomer).

IR(KBr)cm$^{-1}$: 3400, 2970, 1790, 1720, 1680, 1530, 1370, 1150

NMR(DMSO-d$_6$)δ: 1.45(9H, s), 3.50 and 3.72(2H, ABq, J=15 Hz), 3.90(3H, s), 4.14 and 4.36(2H, ABq, J=15 Hz), 5.06(1H, d, J=5 Hz), 5.10(1H, s), 5.29(1H, s), 5.52 (1H, dd, J=5 and 8 Hz), 6.87(1H, s), 7.30(15H, s), 8.80(1H, br s), 9.76(1H, d, J=8 Hz)

(B) The same operation as in step (B) of Example 17 was conducted by using 630 mg (0.73 mmol) of the compound obtained in the above reaction (A) to obtain 195.5 mg (yield: 43.9%) of the above-identified compound.

mp: 155°-160° C. (decomposed)

IR(KBr)cm$^{-1}$: 3400, 1765, 1600, 1540, 1400, 1210

NMR(D$_2$O)δ: 3.43 and 3.82(2H, ABq, J=19 Hz), 4.06(3H, s), 4.20(2H, ABq), 5.20(1H, d, J=5 Hz), 5.22(1H, s), 5.37 (1H, s), 5.83(1H, d, J=5 Hz), 7.18(1H, s)

Example 20

Preparation of trisodium 7β-[2-(2-aminothiazol-4-yl)-2-(1-carboxylato-1-vinyloxyimino)acetamido]-3-(1-carboxylatomethyl-1H-tetrazol-5-yl)thiomethyl-3-cephem-4-carboxylate (syn-isomer)

(A) The same operation as in step (A) of Example 17 was conducted by using 841 mg (1.51 mmol) of 2-(1-tert-butoxycarbonyl-1-vinyloxyimino)-2-(2-tritylaminothiazol-4-yl)acetic acid (syn-isomer) and 745 mg (2 mmol) of 7β-amino-3-(1-carboxymethyl-1H-tetrazol-5-yl)thiomethyl-3-cephem-4-carboxylic acid to obtain 300 mg (yield: 21.9%) of 7β-[2-(1-tert-butoxycarbonyl-1-vinyloxyimino)-2-(2-tritylaminothiazol-4-yl)acetamido]-3-(1-carboxymethyl-1H-tetrazol-5-yl)thiomethyl-3-cephem-4-carboxylic acid (syn-isomer).

IR(KBr)cm$^{-1}$: 3400, 2970, 1785, 1720, 1640, 1590, 1570, 1150, 1040

NMR(DMSO-d$_6$)δ: 1.45(9H, s), 3.60(2H, br), 4.13 and 4.43 (2H, ABq, J=15 Hz), 5.05(1H, d, J=5 Hz), 5.20(2H, s), 5.25(2H, s), 5.30(1H, s), 5.43(1H, s), 5.60(1H, dd, J=5 and 8 Hz), 6.95(1H, s), 7.40 15H, s), 9.46 (1H, br s), 9.75(1H, d, J=8 Hz)

(B) The same operation as in step (B) of Example 17 was conducted by using 260 mg (0.29 mmol) of the compound obtained in the above reaction (A) to obtain 97.1 mg (yield: 50.2%) of the above-identified compound.

mp: 157°-162° C. (decomposed)

IR(KBr)cm$^{-1}$: 3400, 1760, 1620, 1540, 1400, 1210

NMR(D$_2$O)δ: 3.43 and 3.80(2H, ABq, J=17 Hz), 4.08 (2H, ABq), 5.05(2H, s), 5.19(1H, d, J=5 Hz), 5.21(1H, s), 5.33(1H, s), 5.83(1H, d, J=5 Hz), 7.20 (1H, s)

Example 21

Preparation of 7β-[2-(2-aminothiazol-4-yl -2-(1-carboxy-1-vinyloxyimino)acetamido]-3-chloromethyl-3-cephem-4-carboxylic acid trifluoroacetate (syn-isomer)

210 mg (0.23 mmol) of benzhydryl 7β-[2-(1-tert-butoxycarbonyl-1-vinyloxyimino)-2-(2-tritylaminothiazol-4-yl)acetamido]-3-chloromethyl-3-cephem-4-carboxylate (syn-isomer) obtained in step (A) of Example 1, was dissolved in 5 ml of methylene chloride and 1 ml of anisole. 5 ml of trifluoroacetic acid was added thereto under cooling with ice. The mixture was stirred for 1.5 hours. The solvent was distilled off under reduced pressure, and to the residue, 20 ml of diisopropyl ether was added. The precipitated powder was collected by filtration and dried to obtain 115 mg (yield: 83.8%) of the above-identified compound.

mp: 130° C. (decomposed)

IR(KBr)cm$^{-1}$: 3400, 1780, 1660, 1630, 1190, 1000

NMR(DMSO-d$_6$)δ: 3.60(2H, br s), 4.55(2H, br s), 5.18 (1H, d, J=5 Hz), 5.46(2H, br s), 5.80(1H, dd, J=5 and 9 Hz), 7.02(1H, s), 9.82(1H, d, J=9 Hz)

Example 22

Preparation of 2-(1-tert-butoxycarbonyl-1-vinyloxyimino)-2-(2-tritylaminothiazol-4-yl)acetic acid (syn-isomer)

6.03 g (20.8 mmol) of N-(1-tert-butoxycarbonyl-1-vinyloxy)phthalimide prepared in accordance with the method disclosed in British Patent No. 1,602,725, was dissolved in a mixed solution of 200 ml of methylene chloride and 10 ml of methanol. Then, a solution of 1.88 ml of 80% hydrazine hydrate in 40 ml of methanol was dropwise added thereto. The mixture was stirred at room temperature for 1.5 hours. The insolubles were removed, and then the filtrate was washed three times with 8% aqueous ammonia and with a saturated sodium chloride aqueous solution and dried over anhydrous sodium sulfate. The solvent was distilled off under reduced pressure to obtain a residue of O-(1-tert-butoxycarbonyl-1-vinyl)hydroxylamine. The residue was dissolved in 120 ml of methanol, and 7.46 g (18 mmol) of 2-(2-tritylaminothiazol-4-yl)glyoxylic acid was added thereto, and the mixture was stirred at room temperature for three hours. The precipitated crystals were collected by filtration to obtain 7.08 g (yield: 70.9%) of the above-identified compound.

mp: 110°-115° C.(decomposed)

IR(KBr)cm$^{-1}$: 3400, 2970, 1725, 1630, 1100, 700

NMR(DMSO-d$_6$)δ: 1.45(9H, s), 5.20(1H, br s), 5.33 (1H, br s), 7.05(1H, s), 7.10-7.40(15H, m), 8.82 (1H, br s)

Elemental analysis value: as $C_{31}H_{29}N_3O_6S$;

Calculated value (%): C 67.00; H 5.26; N 7.56; S 5.77;

Formed value (%): C 67.00; H 5.58; N 6.74; S 5.54.

Example 23

Preparation of 2-(1 tert-butoxycarbonyl-1-vinyloxyimino)-2-(2-tritylaminothiazol-4-yl)acetic acid (syn-isomer)

392 mg (1.3 mmol) of N-(1-tert-butoxycarbonyl-1-vinyloxy)phthalimide was dissolved in a mixed solution of 8 ml of methylene chloride and 0.8 ml of methanol, and then a solution of 0.165 ml (2.6 mmol) of 80% hydrazine hydrate and 2 ml of methanol was dropwise added thereto. The mixture was stirred at room temperature for 1 hour. The insolubles were removed, and then the filtrate was washed three times with 8% aqueous ammonia and with a saturated sodium chloride aqueous solution and dried over anhydrous sodium sulfate. The solvent was distilled off under reduced pressure to obtain a residue of O-(1-tert-butoxycarbonyl-1-vinyl)hydroxylamine. The residue was dissolved in 5 ml of methanol, and then 414 mg (1.0 mmol) of 2-(2-tritylaminothiazol-4-yl)glyoxylic acid was added thereto. The mixture was stirred at room temperature for 2 hours. The precipitated crystals were collected by filtration to obtain 400 mg (yield: 76.1%) of the above-identified compound. The IR and NMR spectra of the product completely agreed with those of the product of Example 22.

Example 24

Preparation of 2-(2-aminothiazol-4-yl)-2-(1-tert-butoxycarbonyl-1-vinyloxyimino)acetic acid (syn-isomer)

The same operation as in Example 22 was conducted by using 172 mg (1.0 mmol) of 2-(2-aminothiazol-4-yl)glyoxylic acid to obtain 207.5 mg (yield: 66.2%) of the above-identified compound.

mp: 120° C. (decomposed)
IR(KBr)cm$^{-1}$: 3400, 3150, 2990, 1720, 1640, 1380, 1320, 1200, 1150, 980, 850, 730
NMR(DMSO-d$_6$/CD$_3$OD)δ: 1.48(9H, s), 5.29(1H, s), 5.39 (1H, s), 7.10(1H, s), 7.30(2H, br s)

Example 25

Preparation of 2-(1-tert-butoxycarbonyl-1-vinyloxyimino)-2-(2-formamidethiazol-4-yl)acetic acid (syn-isomer)

The same operation as in Example 22 was conducted by using 200 mg (1.0 mmol) of 2-(2-formamidothiazol-4-yl)glyoxylic acid to obtain 183 mg (yield: 53.6%) of the above-identified compound.

mp: 130° C. (decomposed)
IR(KBr)cm$^{-1}$: 3400, 3150, 2980, 1720, 1690, 1630, 1560, 1400, 1380, 1280, 1210, 1150, 980, 850, 740
NMR(DMSO-d$_6$)6 1.48(9H, s), 5.18(1H, s), 5.24(1H, s), 7.49(1H, s), 8.51(1H, s)

Example 26

Preparation of 2-(2-aminothiazol-4-yl)-2-(1-carboxy-1-vinyloxyimino)acetic acid trifluoroacetate (syn-isomer)

350 mg 0.63 mmol) of 2-(1-tert-butoxycarbonyl-1-vinyloxyimino)-2-(2-tritylaminothiazol-4-yl)acetic acid (syn-isomer) was dissolved in a mixed solution of 4 ml of methylene chloride and 0.8 ml of anisole, and the solution was cooled to 0° C. Then, 4 ml of trifluoroacetic acid as previously cooled to 0° C., was added thereto, and the mixture was stirred at the same temperature for 30 minutes and at room temperature for 1.5 hours. The solvent was distilled off under reduced pressure, and to the oily residue, 20 ml of diisopropyl ether was added. The precipitated powder was collected by filtration and washed with diisopropyl ether to obtain 200 mg (yield: 85.5%) of the above-identified compound.

mp: 110°-115° C. (decomposed)
IR(KBr)cm$^{-1}$: 3400, 3120, 1650, 1630, 1610, 1590, 1190, 1180, 980
NMR(DMSO-d$_6$/D$_2$O)δ: 5.40(1H, s), 5.47(1H, s), 7.15 (1H, s)

REFERENCE EXAMPLES

Reference Example 1

Preparation of O-(1-tert-butoxycarbonyl-1-vinyl)hydroxylamine 602 mg (2.0 mmol) of N-(1-tert-butoxycarbonyl-1-vinyloxy)phthalimide prepared in accordance with the method disclosed in British Patent No. 1,602,725, was dissolved in a mixed solution of 5 ml of methylene chloride and 0.5 ml of methanol. Then, a solution of 0.25 ml (5 mmol) of hydrazine hydrate and 0.5 ml of methanol was dropwise added thereto under cooling with ice, and the mixture was stirred at room temperature for 1.5 hours. The solvent was distilled off under reduced pressure, and to the residue, 20 ml of ethyl acetate was added. The mixture was washed twice with 8% aqueous ammonia and twice with a saturated sodium chloride aqueous solution and dried over anhydrous sodium sulfate. The solvent was distilled off under reduced pressure to obtain 260 mg (yield: 78.5%) of the above-identified compound.

IR(KBr)cm$^{-1}$: 3300, 2970, 1720, 1640, 1370, 1330, 1220, 1150
NMR(DMSO-d$_6$)δ: 1.50(9H, s), 5.18(1H, s), 5.25(1H, s), 6.10(2H, br s)

Reference Example 2

Preparation of 2-mercapto-5-[3,4-di(2-methoxyethoxymethoxy)-phenyl]-1,3,4-oxadiazole (A) 2.5 g (14.9 mmol) of methyl protocatechuate was suspended in 50 ml of methylene chloride, and 7.84 ml (45 mmol) of N-ethyldiisopropylamine was added thereto at 0° C. to obtain a homogeneous solution. 5.8 ml (45 mmol) of 2-methoxyethoxymethyl chloride was dropwise added thereto, and the mixture was stirred for 30 minutes. Then, the reaction solution was washed sequentially with water, with a 0.5N sodium hydroxide aqueous solution and with a saturated sodium chloride aqueous solution. Further, the aqueous layer was extracted twice with methylene chloride. The extract and the organic layer were put together and dried over anhydrous sodium sulfate. Then, the solvent was distilled off under reduced pressure to obtain 5.1 g (yield: 99%) of methyl 3,4-di(2-methoxyethoxymethoxy)benzoate.

NMR(CDCl$_3$)δ: 3.32(3H, s), 3.34(3H, s), 3.55(4H, m), 3.83(4H, m), 3.86 3H, s), 5.32(4H, m), 7.18(1H, d, J=9 Hz), 7.67(1H, dd, J=2 and 9 Hz), 7.79 (1H, d, J=2 Hz)

(B) 5.1 g (15 mmol of the compound obtained in the above reaction (A) was dissolved in 100 ml of methanol, and 40 ml (300 mmol) of 80% hydrazine hydrate was added thereto. The mixture was refluxed under heating for 1 hour. Then, 40 ml of 80% hydrazine hydrate was further added thereto, and the mixture was again refluxed under heating for 2 hours. The reaction solution was cooled, then poured into water and extracted twice with ethyl acetate. The extract was washed with a saturated sodium chloride aqueous solution and then dried over anhydrous sodium sulfate. The solvent was distilled off under reduced pressure to obtain 4.2 g of crude 3,4-di(2-methoxyethoxymethoxy)benzohydrazide.

(C) To 42 ml of an ethanol solution containing 1.27 g of 80% potassium hydroxide (18 mmol; 1.0 g of potassium hydroxide and 0.27 ml of water), 4.2 g (12 mmol) of the compound obtained in the above reaction (B) and 3.64 ml (61 mmol) of carbon disulfide were added, and the mixture was refluxed under heating for 1 hour. The solvent was distilled off under reduced pressure. Then, the residue was dissolved in water, and the solution was adjusted to pH 1.5 with 1N hydrochloric acid and extracted three times with ethyl acetate. The organic layer was washed with a saturated sodium chloride aqueous solution and then dried over anhydrous sodium sulfate. The solvent was distilled off under reduced pressure, and the residue was subjected to silica gel column chroamtography (Wakogel C-300, ethyl acetate/hexane=3/1) to obtain 3.03 g (yield: 52.3%) of the above-identified compound.

MP: 84° C.

IR(KBr)cm$^{-1}$: 1620, 1585, 1520, 1500, 1360, 1250, 1105, 1090, 995

NMR(DMSO-d$_6$)δ: 3.27(6H, s), 3.51(4H, m), 3.80(4H, m), 5.38(2H, s), 5.39(2H, s), 7.32(1H, d, J=6 Hz), 7.54 (1H, dd, J=1.8 and 6 Hz), 7.62(1H, d, J=1.8 Hz)

Elemental analysis value: as C$_{16}$H$_{22}$N$_2$O$_7$S;
Calculated value (%): C 49.73; H 5.74; N 7.25; S 8.30;
Found value (%): C 49.66; H 5.85; N 7.10; S 8.24.

Reference Example 3

Preparation of 2-mercapto-5-[3,4-di(2-methoxyethoxymethoxy)-phenyl]-1,3,4-thiadiazole (A) 15.0 g (50.7 mmol) of 3,4-di(2-methoxyethoxymethoxy)benzonitrile was dissolved in 15.0 ml of pyridine, and 7.5 ml (50 mmol) of triethylamine was added thereto. To this solution, hydrogen sulfide gas was introduced and stirred at room temperature for 6 hours. To the reaction solution, ethyl acetate and water were added. The organic layer was separated and then dried over anhydrous sodium sulfate. The solvent was distilled off under reduced pressure to obtain 18.8 g (yield: 100%) of crude 3,4-di(2-methoxyethoxymethoxy)thiobenzamide. The product was used for the subsequent reaction without purification.

IR(KBr)cm$^{-1}$: 3320, 3200, 2900, 1635, 1515

(B) 2.0 g (5.8 mmol) of the compound obtained in the above reaction (A) was dissolved in 20.0 ml of ethanol, and 0.40 ml of hydrazine hydrate was added thereto. The mixture was stirred at 70° C. for 1 hour. To the reaction solution, 0.40 g (5.70 mmol) of potassium hydroxide and 1.38 ml (18 mmol) of carbon disulfide were added, and the mixture was refluxed for 20 minutes. The solvent was distilled off under reduced pressure. The residue was dissolved in water and washed with ethyl acetate. The aqueous layer was adjusted to pH 3.0 with 2N hydrochloric acid, then extracted with ethyl acetate and dried over anhydrous sodium sulfate. The solvent was distilled off under reduced pressure, and the crystal residue was washed with diethyl ether to obtain 0.94 g (yield: 40%) of the above-identified compound.

IR(KBr)cm$^{-1}$: 3160, 2500, 1600, 1585, 1510, 1455

NMR(DMSO-d$_6$)δ: 3.25(6H, s), 3.50(4H, m), 3.78(4H, m), 5.34(4H, br s), 7.26(1H, d, J=8 Hz) 7.33(1H, dd, J=1 and 8 Hz), 7.52(1H, d, J=1 Hz)

Elemental analysis value (%): as C$_{16}$H$_{22}$N$_2$O$_6$S$_2$;
Calculated value: C 47.75; H 5.51; N 6.96; S 15.93;
Found value: C 47.75; H 5.44; N 6.94; S 15.72.

Reference Example 4

Preparation of 5-3,4-dihydroxyphenyl)-2-mercapto-1,3,4-thiadiazole (A) 10 g (178 mmol) of potassium hydroxide was dissolved in 400 ml of ethanol, and 20 g (119 mmol) of protocatechuhydrazide was added thereto under stirring at a temperature of at most 5° C. To this solution, 28.0 ml of carbon disulfide was dropwise added over a period of 10 minutes at a temperature of at most 10° C., and the mixture was stirred at a temperature of from 0° to 10° C. for 30 minutes. Then, the precipitates were collected by filtration, washed with ethanol and dried to obtain 25.3 g (yield: 75.3%) of potassium 3-protocatechuoyldithiocarbazate.

(B) 25.3 g (89.6 mmol) of the compound obtained in the above reaction (A) was gradually added to 125 ml of concentrated sulfuric acid over a period of 20 minutes at a temperature of at most 10° C. Then, the mixture was stirred at 10° C. for 20 minutes. The reaction solution was gradually added to 600 g of ice and 300 ml of water, and then the mixture was further stirred for 10 minutes. The precipitates were collected by filtration and dissolved in 125 ml of acetone. 600 ml of ethyl acetate, 20 ml of water and 1 g of activated carbon were added thereto, and the mixture was stirred for 15 minutes. The activated carbon was removed by filtration, and then the filtrate was washed sequentially with 200 ml of a 5% sodium thiosulfate aqueous solution, with 150 ml of water and with a saturated sodium chloride aqueous solution. The organic layer was dried over anhydrous magnesium sulfate, and the solvent was distilled off. The crystal residue was washed with diethyl ether to obtain 3.6 g (yield: 17.8%) of the above-identified compound.

IR(KBr)cm$^{-1}$: 3600–2000, 1650, 1600, 1430, 1300, 1250

NMR(DMSO-d$_6$)δ: 6.82(1H, d, J=9 Hz), 7.01(1H, dd, J=2 and 9 Hz), 7.13(1H, d, J=2 Hz), 9.50(2H, br s), 14.38(1H, br s)

Reference Example 5

Preparation of 4-(3,4-dihydroxyphenyl)-2-mercaptothiazole 10.0 g (53.6 mmol) of 2-chloro-3'4'-dihydroxyacetophenone was dissolved in 100 ml of methanol, and then 5.90 g (53.6 mmol) of ammonium dithiocarbamate was added thereto. The mixture was stirred at room temperature for 30 minutes. The solvent was distilled off under reduced pressure. To the residue, water was added to adjust the mixture to pH2.0, and then the mixture was extracted twice with ethyl acetate. The extract was dried over anhydrous sodium sulfate and-then concentrated. The crystal residue was washed with diethyl ether to obtain 8.80 g (yield: 72.9%) of the above-identified compound.

MP: 236° C. (solvent for recrystallization: ethyl acetate)

IR(KBr)cm$^{-1}$: 3240, 1615, 1525, 1470

NMR(DMSO-d$_6$)δ: 6.77(1H, d, J=9 Hz), 6.92(1H,s), 7.03(1H, dd, J=2 and 9 Hz), 7.08(1H, d, J=2 Hz), 9.15(1H, m)

Elemental analysis value: as C$_9$H$_7$NO$_2$S$_2$; Calculated value (%): C 47.98; H 3,13; N 6.21; S 28.47; Found value (%): C 48.07; H 3.02; N 6.22; S 28.16.

Reference Example 6

Preparation of 4-carboxy-5-(3,4-dihydroxyphenyl)-2-mercaptothiazole (A) 60.1 g of piperonal as a starting material was treated in the same manner as the method disclosed in Org. Syn., Coll. Vol. II, p.1-3, p.11-12 and p.519-520 to obtain 48.3 g (yield: 58%) of 3-(3,4-methylenedioxyphenyl) pyruvic acid.

IR(KBr)cm$^{-1}$: 1670, 1500, 1490, 1450, 1250, 1040

NMR(DMSO-d$_6$)δ: 6.03(2H, s), 6.38(1H, s), 6.87(1H, d, J=7.5 Hz), 7.23(1H, d, J=7.5 Hz), 7.46(1H, s), 9.00(2H, s)

(B) 10.4 g (0.05 mol) of the compound obtained in the above reaction (A) was suspended in 100 ml of ethyl acetate, and 2.56 ml (0.05 mol) of bromine was added thereto at −10° C. The mixture was stirred at the same temperature for 30 minutes. To the reaction solution, 200 ml of ethanol was added, and 9.92 g (0.09 mol) of ammonium dithiocarbanate was added thereto at −10° C. The mixture was stirred at the same temperature for 20 minutes and at room temperature for 2 hours. The reaction solution was cooled in an ice bath for 40 minutes. The insolubles were removed by filtration and washed with 40 ml of ethyl acetate. The filtrate and the washing solution were put together and concentrated under reduced pressure. To the residue, 350 ml of water was added, and the mixture was heated at 80° C. for 18 hours. Then, gummy insolubles were removed by filtration under heating. The filtrate was adjusted to pH1.5 with 6N hydrochloric acid under cooling with ice. The precipitates were collected by filtration, washed with 30 ml of water and dried to obtain 7.23 g of the above-identified compound as yellow powder.

Further, the above gummy insolubles were suspended in 20 ml of acetone. The insolubles were collected by filtration and dried to obtain 1.02 g of the secondary crystals. Total amount: 8.25 g (yield: 66%).

IR(KBr)cm$^{-1}$: 1710, 1690, 1500, 1490, 1450, 1430, 1320, 1260, 1060, 1040

NMR(DMSO-d$_6$)δ: 6.10(2H, s), 6.97(2H, s), 7.12(1H, s), 12.0-15.0(2H, br s)

(c) 6.79 g (0.024 mol) of the compound obtained in the above reaction (B) was suspended in 180 ml of methylene chloride, and 13 ml of ethanethiol, and 16.0 g (0.12 mol) of anhydrous aluminum chloride was added thereto at 5° C. The mixture was stirred at the same temperature for 4 hours and at 10° C. for 24 hours. 100 ml of 6N hydrochloric acid was dropwise added thereto under cooling with ice, and then the mixture was stirred at the same temperature for 1.5 hours. The insolubles were collected by filtration, washed twice with 50 ml of water and dried to obtain 5.35 g of a crude product. The crude product was recrystallized from a solvent mixture of methanol/water to obtain 3.93 g (yield: 61%) of the above-identified compound as yellow needle crystals.

MP: 245°–247° C. (decomposed)

IR(KBr)cm$^{-1}$: 1710, 1700, 1610, 1520, 1480, 1350, 1300, 1250, 1210, 1190, 1120, 1070, 1010

NMR(DMSO-d$_6$)δ: 5.00–7.50(2H, br s), 6.79(2H, s), 6.90(1H, s), 8.00–10.0(2H, br s) 1% 309.5(480), 340.5(481)

Reference Example 7

Preparation of 4-(3,4-diacetoxyphenyl)-5-benzhydryloxycarbonylmethyl-2-mercaptothiazole (A) 70 g (0.7 mol) of succinic anhydride and 96.6 g (0.7 mol) of veratrole were dissolved in 2,000 ml of methylene chloride, and 237 g (1.75 mol) of anhydrous aluminum chloride was added thereto at room temperature. The mixture was stirred at the same temperature for 6 hours. The reaction solution was left to stand for 15 hours. Then, 1,600 ml of 6N hydrochloric acid was dropwise added to the reaction solution under stirring and the mixture was further stirred for one hour. The organic layer was separated, and 300 ml of water was added thereto. The mixture was adjusted to pH7.5 with a saturated sodium bicarbonate aqueous solution. The aqueous layer was separated and adjusted to pH2.5 with 6N hydrochloric acid. The aqueous layer was left to stand in a refrigerator for two days. Then, the precipitated crystals were collected by filtration, washed with water and dried to obtain 106.8 g (yield: 64%) of 3-(3,4-dimethoxybenzoyl)propionic acid.

IR(KBr)cm$^{-1}$: 3360, 1740, 1665, 1590, 1515, 1415, 1335, 1270, 1150, 1020, 800, 770, 610

NMR(DMSO-d$_6$)δ: 2.56(2H, t, J=6.0 Hz), 3.21(2H, t, J=6.0 Hz), 3.93(3H, s), 3.95(3H, s), 7.04(1H, d, J=8.7 Hz), 7.45(1H, d, J=1.5 Hz), 7.67(1H, dd, J=1.5 and 4.5 Hz), 11.0–12.5(1H, br)

(B) To 106 g (0.445 mol) of the compound obtained in the above reaction, 1,070 ml of 48% hydrobromic acid was added, and the mixture was refluxed at a boiling-point for 5 hours. The solvent was distilled off under reduced pressure. To the residue, 1,000 ml of water was added and the residue was dissolved under heating. Then, the solution was subjected to treatment by an activated carbon. The filtrate was kept under cooling overnight to obtain blackish brown crystals. This colored crystals were dissolved in 1,000 ml of water under heating, and the solution was subjected to treatment by an activated carbon twice. Then, the solution was kept under cooling overnight to obtain 37.2 g (yield: 39.8%) of 3-(3,4-dihydroxybenzoyl)propionic acid as colorless plates.

IR(KBr)cm$^{-1}$: 3460, 3370, 1740, 1660, 1590, 1405, 1380, 1245, 1165, 1125, 885, 820, 610

NMR(DMSO-d$_6$)δ: 2.53(2H, t, J=6.2 Hz), 3.12(2H, t, J=6.2 Hz), 6.82(1H, d, J=8.7 Hz), 7.30–7.50(2H, m), 9.00–10.50(2H, br), 11.30–12.80(1H, br)

(C) To 2.0 g (9.52 mmol) of the compound obtained in the above reaction (B), 9.0 ml of acetic anhydride and 0.78 g (9.5 mmol) of sodium acetate were added, and the mixture was refluxed under heating for 30 minutes. The solvent was distilled off under reduced pressure, and to the residue, ethyl acetate was added. The mixture was washed with a 5% sodium bicarbonate aqueous solution and then dried over anhydrous magnesium sulfate. The solvent was distilled off under reduced pressure, and the residue was purified by silica gel column chromatography (Wakogel C-300, 2% methanol/methylene chloride) to obtain 1.33 g (yield: 50%) of 4-(3,4-diacetoxyphenyl)-2(3H)-furanone.

NMR(DMSO-d$_6$)δ: 2.30 6H, s), 3.58(2H, m), 6.24(1H, m), 7.30–7.60(3H, m)

(D) 300 mg (1.08 mmol) of the compound obtained in the above reaction (C)--was dissolved in 8 ml of a mixed solvent of dioxane/water (3/1), and 193 mg of N-bromosuccinimide was added thereto at room temperature. The mixture was stirred for 15 minutes. The reaction solution was poured into ethyl acetate, and the organic layer was dried over anhydrous magnesium sulfate. Then, to the filtrate, 300 mg (1.54 mmol) of diphenyldiazomethane was added, and the mixture was stirred for one hour. The solvent was distilled off under reduced pressure, and the residue was purified by silica gel column chromatography (Wakogel C-300, ethyl acetate/hexane =1/3) to obtain 350 mg (yield: 60%) of benzhydryl 3-(3,4-diacetoxybenzoyl)-3-bromopropionate.

NMR(DMSO-d$_6$)δ: 2.33(6H, s), 3.20–3.80(2H, m), 6.00(1H, t, J=8.0 Hz), 6.80(1H, s), 7.10–7.60(13H, m)

(E) 700 mg (1.30 mmol) of the compound obtained in the above reaction was dissolved in 7.0 ml of N,N-dimethylformamide, and 143 mg (1.30 mmol) of ammonium dithiocarbamate was added thereto under cooling with ice. The mixture was stirred for 15 minutes. The solvent was distilled off under reduced pressure, and the residue was purified by silica gel column chromatography (Wakogel C-300, ethyl acetate/hexane=½) to obtain 470 mg (yield: 68%) of the above-identified compound.

IR(KBr)cm⁻¹: 3400, 3240, 1750, 1735, 1500, 1470, 1370, 1260, 1200, 1160, 1050

NMR(DMSO-d$_6$)δ: 2.30(6H, s), 3.00(2H, m), 4.40(1H, br t, J=7.0 Hz), 6.78.(1H, s), 7.10–7.60(13H, m)

Reference Example 8

Preparation of 5-(3,4-dihydroxyphenyl)-2-mercaptooxazole (A) 10 g (53.6 mmol) of 2-chloro-3',4'-dihydroxyacetophenone was dissolved in 50 ml of acetone, and 600 mg (4.0 mmol) of sodium iodide and 5.23 g (80.5 mmol) of sodium azide were added thereto. The mixture was refluxed for 24 hours. The insolubles in the reaction solution were removed by filtration, and the filtrate was concentrated under reduced pressure. To the reaction solution, ethyl acetate was added, and the mixture was washed sequentially with water and with a saturated sodium chloride aqueous solution and dried over anhydrous sodium sulfate. The solvent was distilled off under reduced pressure, and the oily residue was dissolved in 100 ml of methanol and 13.6 ml of concentrated hydrochloric acid. 1.5 g of 10% palladium carbon catalyst was added to the solution, and the mixture was stirred under heating at 40° C. under a hydrogen gas stream for 5 hours. The reaction solution was filtered, and the filtrate was concentrated under reduced pressure. To the concentrated residue, acetone was added, and the precipitated crystals were collected by filtration to obtain 5.5 g (yield: 50.4%) of 2-amino-3',4'-dihydroxyacetophenone hydrochloride.

NMR(DMSO-d$_6$(D$_2$O))δ: 4.40(2H, s), 6.90(1H, d, J=9.0 Hz), 7.30–7.50(2H, m)

(B) 1.0 g (4.9 mmol) of the compound obtained in the above reaction (A) was suspended in 17 ml of an ethanol solution of 0.043N sodium ethoxide, and 2.1 ml (35 mmol) of carbon disulfide was added thereto. The mixture was stirred at 60° C. for 20 hours. The reaction solution was poured into 50 ml of water, and the mixture was adjusted to pH1.5 with 6N hydrochloric acid. The mixture was stirred for one hour and then extracted with ethyl acetate. The organic layer was washed sequentially with water and with a saturated sodium chloride aqueous solution and dried over anhydrous sodium sulfate. The solvent was distilled off under reduced pressure to obtain 750 mg (yield: 73%) of the above-identified compound.

MP: 215°–8° C.

IR(KBr)cm⁻¹: 1640, 1600, 1520, 1500, 1300, 1180, 1120

NMR(DMSO-d$_6$/D$_2$O)δ: 6.70–6.95(2H, m ), 7.00(1H, s), 7.42(1H, s),

Elemental analysis value: as C$_9$H$_7$NO$_3$S; Calculated value: C 51 12; H 3.12; N 6.43; Found value: C 51,67; H 3.37; N 6.69.

Reference Example 9

Preparation of 2-mercapto-5,6-di(2-methoxyethoxymethoxy)benzimidazole (A) 10 g (44 mmol) of 4,5-dimethoxy-1,2-dinitrobenzene was suspended in 150 ml of 45% hydrobromic acid, and the suspension was refluxed at a boiling point for 6 hours. The reaction solution was allowed to cool to room temperature, and 500 ml of water was added thereto. The mixture was extracted three times with ethyl acetate. The organic layer was washed with a 10% sodium bicarbonate aqueous solution and dried over anhydrous sodium sulfate. The solvent was distilled off under reduced pressure. The crystal residue was washed with methylene chloride to obtain 7 g (yield: 79%) of 4,5-dihydroxy1,2-dinitrobenzene.

NMR(DMSO-d$_6$)δ: 7.48(2H, s), 8.50(2H, br s)

(B) 28 g (0.14 mol) of the compound obtained in the above reaction (A) was suspended in 280 ml of methylene chloride, and 30 ml (0.42 mol) of ethyl diisopropylamine was added thereto at room temperature and dissolved. To the reaction solution, 30 ml (0.42 mol) of 2-methoxyethoxymethyl chloride was dropwise added at 0° C., and the mixture was stirred for 30 minutes. The reaction solution was poured into water. The organic layer was washed with a 1N sodium hydroxide aqueous solution, with a saturated sodium chloride aqueous solution and dried over anhydrous sodium sulfate. The solvent was distilled off under reduced pressure to obtain 39 g (yield: 74%) of 4,5-di(2-methoxyethoxymethoxy)-1,2-dinitrobenzene.

IR(KBr)cm⁻¹: 2900, 1525, 1362

NMR(DMSO-d$_6$)δ: 3.23(6H, s), 3.50(4H, m), 3.78(4H, m) 5.58(4H, s), 8.01(2H, s)

(C) 9.5 g (25 mmol) of the compound obtained in the above reaction (B) was dissolved in 180 ml of ethanol, and 1 g of a 10% palladium carbon catalyst was added thereto. Catalytic hydrogenation was conducted at 80° C. for 2 hours. 1 g of an additional 10% palladium carbon catalyst was added to the reaction solution, and the catalytic hydrogenation was conducted under the same condition (this operation was repeated twice). The catalyst was removed by filtration, and the filtrate was concentrated under reduced pressure. The residue was subjected to silica gel column chromatography (Wakogel C-300, ethyl acetate/hexane=1/1). The eluted fraction containing the desired compound was concentrated to obtain 5.07 g (yield: 57%) of 4,5-di 2-methoxyethoxymethoxy)-2-nitroaniline (the product was unstable, therefore promptly used for the subsequent reaction).

(D) 3.5 g (10 mmol) of the compound obtained in the above reaction (C) was dissolved in 70 ml of ethanol, and 0.6 g of a 10% palladium carbon catalyst was added thereto. The catalytic hydrogenation was conducted at 80° C. for one hour. 0.6 g of an additional 10% palladium catalyst was further added to the reaction solution, and the reduction reaction was conducted under the same condition (this operation was repeated twice). The catalyst was removed by filtration, and then to the filtrate, 10 g (6.1 mmol) of potassium O-ethyl dithiocarbonate and 3 ml of water were added. The mixture was refluxed at a boiling point for three hours. The solvent was distilled off under reduced pressure. The residue was dissolved in water, and the solution was adjusted to pH3.0 with acetic acid and extracted three times with ethyl acetate. The organic layer was dried and concentrated under reduced pressure. The residue was subjected to silica gel column chromatography (Wakogel C-300, ethyl acetate/hexane=3/1). The eluted fraction containing the desired compound was concentrated to obtain 2-mercapto-5,6-di(2-methoxyethoxymethoxy)-benzimidazole (yield: 61%).

IR(KBr)cm⁻¹: 3280, 1622, 1475, 1322

NMR(DMSO-d$_6$)δ: 3.25 (6H, s), 3.32(2H, s), 3.48(4H, m), 3.75(4H, m), 5.20(4H, s), 6.94(2H, s)

Reference Example 10

Preparation of 2-mercapto-5,6-di(2-methoxyethoxymethoxy)-1-methylbenzimidazole (A) 1.57 g (4.54 mmol) of 4,5-di(2-methoxyethoxymethoxy)-2-nitroaniline obtained in step (C) of Reference Example 34 was dissolved in 16 ml of N,N-dimethylformamide, and 2 g (8.63 mmol) of silver oxide and 10 ml (160 mmol) of methyl iodide were added thereto. The mixture was stirred at room temperature for one hour. The solvent was distilled off under reduced pressure, and the residue was subjected to silica gel column chromatography (Wakogel C-300, ethyl acetate/hexane=1/1). The eluted fraction containing the desired compound was concentrated to obtain 0.85 g of crude 4,5-di(2-methoxyethoxymethoxy)-N-methyl-2-nitroaniline. (B) 0.85 g of the crude product obtained in the above reaction (A) was dissolved in 16 ml of ethanol, and 0.4 g of a 10% palladium carbon catalyst was added thereto. The catalytic hydrogenation was conducted at 80° C. for two hours. The catalyst was removed by filtration, and then to the filtrate, 1 g (6.25 mmol) of potassium O-ethyl dithiocarbonate was added. The mixture was refluxed at a boiling point for two hours. The reaction solution was concentrated under reduced pressure, and the residue was dissolved in water. The solution was adjusted to pH5.0 with acetic acid and then extracted with ethyl acetate. The organic layer was dried over anhydrous sodium sulfate and the solvent was distilled off under reduced pressure. The residue was subjected to silica gel column chromatography (Wakogel C-300, ethyl acetate/hexane=3/1) to obtain 67 mg of the above-identified compound.

NMR(CDCl₃)δ: 3.40(6H, s), 3.60(4H, m), 3.68(3H, s), 3.88(4H, m), 5.27(2H, s), 5.30(2H, s), 7.02(1H, s), 7.08(1H, s)

Reference Example 11

Preparation of 2-mercapto-5,6-di(2-methoxyethoxymethoxy)benzoxazole (A) 5.4 g (17 mmol) of 3,4-di(2-methoxyethoxymethoxy)benzaldehyde was dissolved in 216 ml of methylene chloride, and 80% m-chloroperbenzoic acid was added thereto. The mixture was refluxed at a boiling point for 20 hours. The reaction solution was washed with a sodium bicarbonate aqueous solution and with a saturated sodium chloride aqueous solution and then dried. The solvent was distilled off under reduced pressure to obtain 4.85 g (yield: 86%) of O-formyl-3,4-di(2-methoxyethoxymethoxy)phenol. The product was used for the subsequent reaction without purification.

NMR(CDCl₃/DMSO-d₆)δ: 3.36(6H, s), 3.58(4H, m), 3.82(4H, m), 5.28(4H, br s), 6.73(1H, dd, J=2 and 9 Hz), 7.02(1H, d, J=2 Hz), 7.29(1H, d, J=9 Hz)

(B) 4.85 g (14.7 mmol) of the compound obtained in the above reaction (A) was dissolved in 4 ml of methanol, and 7.0 ml (17.6 mmol) of 10% sodium hydroxide was added thereto. The mixture was stirred at room temperature for 30 minutes. The reaction solution was poured into 1,000 ml of water, and the mixture was washed with ethyl acetate. The aqueous layer was adjusted to pH5.0 with 6N hydrochloric acid and extracted with ethyl acetate. After drying over anhydrous sodium sulfate, the solvent was distilled off under reduced pressure. The residue was dissolved in 8 ml of acetic acid, and 0.70 ml (11 mmol) of concentrated nitric acid was added thereto at 10° C. The mixture was stirred for 1 hour. The reaction solution was poured into ethyl acetate and washed sequentially with water and with a saturated sodium bicarbonate aqueous solution. The organic layer was dried and concentrated. The residue was subjected to silica gel column chromatography (Wakogel C-300, ethyl acetate/hexane=1/1). The eluted fraction containing the desired compound was concentrated to obtain 1.51 g (yield: 29.6%) of 4,5-di(2-methoxyethoxymethoxy)-2-nitrophenol.

NMR(DMSO-d₆)δ: 3.25(6H, s), 3.50(4H, m), 3.76(4H, m), 5.23(4H, s), 6.87(1H, s), 7.75(1H, s)

(C) 1.5 g (4.3 mmol) of the compound obtained in the above reaction (B) was dissolved in 30 ml of ethanol, and 0.5 g of a 10% palladium carbon catalyst was added thereto. The catalytic hydrogenation was conducted at 70° C. for 1.5 hours. The contact was removed by filtration, and then to the filtrate, 0.36 g (4.73 mmol) of carbon disulfide, 0.35 g (5.0 mmol) of a 80% potassium hydroxide aqueous solution and 0.78 ml (43 mmol) of water were added. The mixture was refluxed at a boiling point for 1.5 hours. The solvent was distilled off under reduced pressure, and the residue was dissolved in water. The solution was adjusted to pH5.0 with 6N hydrochloric acid and then extracted with ethyl acetate. The organic layer was dried and concentrated. The residue was subjected to silica gel column chromatography (Wakogel C-300, ethyl acetate/hexane=1/1) to obtain 857 mg (yield: 55.5%) of the above-identified compound.

NMR(DMSO-d₆)δ: 3.22(6H, s), 3.46(4H, m), 3.75(4H, m), 5.23(4H, s), 7.00(1H, s), 7.34(1H, s)

INDUSTRIAL APPLICABILITY

As aforementioned, the cephalosporin derivatives according to the present invention are useful as antibacterial agents and can be used for the treatment of human infectious diseases caused by sensitive and resistant Gram-positive and Gram-negative bacteria, particularly Gram-negative bacteria including glucose non-fermentative Gram-negative rods such as *Pseudomonas aeruginosa*, *Pseudomomas cepacia*, *Pseudomonas maltophilia* and *Acinetobacter calcoaceticus*.

Further, the 1-carboxy-1-vinyl acetic acid derivatives are useful as the intermediates of said cephalosporin derivatives.

We claim:

1. A compound having the formula:

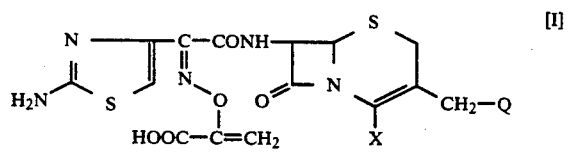

wherein X is COO(−) or COOR, wherein R is a hydrogen atom or a carboxyl-protecting group and Q is a 5- or 6-membered aromatic heterocyclic thio group selected from the group consisting of a thienylthio group, a furylthio group, an imidazolylthio group, a pyrazolylthio group, a thiazolylthio group, an isothiazolylthio group, an oxazolylthio group, an isoxazolylthio group, a triazolylthio group, a thiadiazolylthio group, an oxadiazolylthio group, a tetrazolylthio group, a pyridylthio group, a pyradinylthio group, a pyridadinylthio group, a triazinylthio group, a 2-benzoxazolylthio group, a 2-benzothiazolylthio group and a 2-benzoimidazolylthio group, wherein each of said heterocyclic thio groups may be substituted by one or more substituents which may be the same or different, selected from the group consisting of a hydroxyl group, a $C_{1-6}$ alkoxy group, a formyloxy group, an alkanoyloxy group, a carbamoyloxy group, a carboxyl group, a $C_{1-6}$ alkoxycarbonyl group, a carbamoyl group, a cyano group, a sulfo group, a sulfamoyl group, an amino group, a di($C_{1-6}$ alkyl)amino group, a halogen atom and an aryl and a 5- or 6-membered aromatic heterocyclic group selected from the group consisting of a phenyl group, a naphthyl group, a thienyl group, a furyl group, an imidazolyl group, a pyrazolyl group, a thiazolyl group, an isothiazolyl group, an oxazolyl group, an isoxazolyl group, a triazolyl group, a thiadiazolyl group, an oxadiazolyl group, a tetrazolyl group, a pyridyl group, a pyrazinyl group, a pyridazinyl group and a triazinyl group, provided that each of said aryl and 5- or 6-membered aromatic heterocyclic groups may be substituted by one or more substituents which may be the same or different, selected from the group consisting of a $C_{1-6}$ alkyl group, a $C_{2-6}$ alkenyl group, a $C_{2-3}$ alkynyl group, a fluoro $C_{1-6}$ alkyl group, a hydroxyl group, a $C_{1-6}$ alkoxy group, a formyl group, an alkanoyloxy group, a carbamoyloxy group, a di($C_{1-6}$ alkyl)carbamoyloxy group, a carboxyl group, a $C_{1-6}$ alkoxycarbonyl group, a carbamoyl group, a cyano group, a sulfo group, an acetamido group, a sulfamoyl group, an amino group, a di($C_{1-6}$ alkyl)amino group, an oxyimino group, a methoxyimino group, an ethoxyimino group, a halogen atom and a phenyl, an oxazolyl, a thiazolyl, an oxadiazolyl and a tetrazolyl group which may be substituted by one or more substituents selected from the group consisting of a hydroxyl group, an acetoxy group and a carbamoyloxy group, or a non-toxic salt or physiologically hydrolyzable non-toxic ester thereof.

2. The compound according to claim 1, wherein Q is a 5- or 6-membered aromatic heterocyclic thio group selected from the group consisting of a thienylthio group, a furylthio group, an imidazolylthio group, a pyrazolylthio group, a thiazolylthio group, an isothiazolylthio group, an oxazolylthio group, an isoxazolylthio group, a triazolylthio group, a thiadiazolylthio group, an oxadiazolylthio group, a tetrazolylthio group, a pyridylthio group, a pyridinylthio group, a pyridadinylthio group, a triazinylthio group, a 2-benzoxazolylthio group, a 2-benzothiazolylthio group and a 2-benzoimidazolylthio group, wherein each of said hetercyclic thio groups may be substituted by one or more substituents which may be the same or different, selected from the group consisting of a hydroxyl group, a $C_{1-6}$ alkoxy group, a formyl group, an alkanoyl group, a carbamoyloxy group, a di($C_{1-6}$ alkyl)carbamoyloxy group, a carboxyl group, a $C_{1-6}$ alkoxycarboxy group, a carbamoyl group, a cyano group, a sulfo group, an acetamido group, a sulfamoyl group, an amino group, a di($C_{1-6}$ alkyl)amino group, a halogen atom and a phenyl, an oxazolyl, a thiazolyl, an oxadiazolyl and a tetrazolyl group which may be substituted by one or more substituents which may be the same or different, selected from the group consisting of a hydroxyl group, an acetoxy group and a carbamoyloxy group.

3. The compound according to claim 1, wherein Q is the 5- or 6-membered aromatic heterocyclic thio group and is a thiazolylthio, an oxazolylthio, an isoxazolylthio, a triazolylthio, a thiadiazolylthio, an oxadiazolylthio, a tetrazolylthio or a pyridylthio group which may be substituted by one or more substituents selected from the group consisting of a hydroxyl group, a carboxyl group, a carbamoyl group, a sulfo group and a phenyl group which may be substituted by one or more substituents selected from the group consisting of a hydroxyl group, an acetoxy group and a carbamoyloxy group.

4. The compound according to claim 1, wherein Q is an oxazolylthio, a triazolylthio, a thiadiazolylthio, an oxadiazolylthio or a tetrazolylthio group which may be substituted by one or more substituents selected from the group consisting of a carboxyl group, a carboxy-$C_{1-6}$ alkyl group, a carbamoyl group, a sulfo-$C_{1-6}$ alkyl group, an amino group, a formamido group, a 3,4-dihydroxyphenyl group and a 3,4-diacetoxyphenyl group.

5. The compound according to claim 1, which is, 7β-[2-(2-aminothiazol-4-yl)-2-(1-carboxy-1-vinyloxyimino)acetamido]3-[5-(3,4-dihydroxyphenyl)-1,3,4-oxadiazol-2-yl]thiomethyl-3-cephem-4-carboxylic acid (syn-isomer), 7β-[2-(2-aminothiazol-4-yl)-2-(1-carboxy-1-vinyloxyimino)acetamido]-3-[4-(3,4-dihydroxyphenyl)thiazol-2-yl]thiomethyl-3-cephem-4-carboxylic acid (syn-isomer), 7β-[2-(2-aminothiazol-4-yl)-2-(1-carboxy-1-vinyloxyimino)acetamido]-3-[5-(3,4-dihydroxyphenyl)-1,3,4-thiadiazol-2-yl]thiomethyl-3-cephem-4-carboxylic acid (syn-isomer), 7β-[2-(2-aminothiazol-4-yl)-2-(1-carboxy-1-vinyloxyimino)acetamido]-3-[5-(3,4-dihydroxyphenyl)oxazol-2-yl]thiomethyl-3-cephem-4-carboxylic acid (syn-isomer), 7β-[2-(2-aminothiazol-4-yl)-2-(1-carboxy-1-vinyloxyimino)acetamido]-3-(4-carboxy-5-(3,4-dihydroxyphenyl)thiazol-2-yl]thiomethyl-3-cephem-4-carboxylic acid (syn-isomer), 3-[4-(3,4-diacetoxyphenyl)-5-carboxymethylthiazol-2-yl]thiomethyl-7β-[2-(2-aminothiazol-4-yl)-2-(1-carboxy-1-vinyloxyimino)acetamido]-3-cephem-4-carboxylic acid (syn-isomer), 7β-[2-(2-aminothiazol-4-yl)-2-(1-carboxy-1-vinyloxyimino)acetamido] -3-(1-methyl-1H-tetrazol-5-yl)thiomethyl-3-cephem-4-carboxylic acid (syn-isomer), or 7β-[2-(2-aminothiazol-4-yl)-2-(1-carboxy-1-vinyloxyimino)acetamido]-3-(1-carboxymethyl-1H-tetrazol-5-yl)thiomethyl-3-cephem-4-carboxylic acid (syn-isomer).

6. The compound according to claim 1, wherein said carboxyl-protecting group is t-butyl, 2,2,2-trichloroethyl, acetoxymethyl, propionyloxymethyl, pivaloyloxymethyl, 1-acetoxyethyl, 1-propionyloxyethyl, 1-(ethoxycarbonyloxy)ethyl, phthalidyl, benzyl, 4-methoxybenzyl, 3,4-dimethoxybenzyl, 4-nitrobenzyl, benzhydryl, bis(4-methoxyphenyl)methyl, (5-methyl-2-oxo-1,3-dioxol-4-yl)methyl, trimethylsilyl or p-butyldimethylsilyl.

7. An antibacterial composition comprising an effective amount of a compound as claimed in claim 1, or a non-toxic salt or physiologically hydrolyzable non-toxic ester thereof, in admixture with a pharmaceutically acceptable carrier.

* * * * *

UNITED STATES PATENT AND TRADEMARK OFFICE
CERTIFICATE OF CORRECTION

PATENT NO. : 5,225,406
DATED : July 6, 1993
INVENTOR(S) : Susumu Nakagawa et al.

It is certified that error appears in the above-indentified patent and that said Letters Patent is hereby corrected as shown below:

On the title page, Item [30],

The Foreign Application Priority Data has been omitted, should read:  --Apr. 14, 1987  [PCT]  PCT............PCT/JP87/00236

Apr. 14, 1986  [JP]  Japan............61-84079

May 1, 1986  [JP]  Japan............61-99440

Aug. 5, 1986  [JP]  Japan............61-182809

Dec. 27, 1986  [JP]  Japan............61-309178--

Signed and Sealed this

Fifth Day of April, 1994

Attest:

BRUCE LEHMAN

Attesting Officer

Commissioner of Patents and Trademarks